US007558411B2

(12) United States Patent
Elashoff et al.

(10) Patent No.: US 7,558,411 B2
(45) Date of Patent: Jul. 7, 2009

(54) METHOD AND SYSTEM FOR MANAGING AND QUERYING GENE EXPRESSION DATA ACCORDING TO QUALITY

(75) Inventors: Michael Elashoff, Germantown, MD (US); Chris Alvares, Potomac, MD (US); Peter Lauren, Columbia, MD (US)

(73) Assignee: Ocimum Biosolutions, Inc., Gaithersburg, MD (US)

( * ) Notice: Subject to any disclaimer, the term of this patent is extended or adjusted under 35 U.S.C. 154(b) by 942 days.

(21) Appl. No.: 10/523,499

(22) PCT Filed: Aug. 1, 2003

(86) PCT No.: PCT/US03/24160

§ 371 (c)(1),
(2), (4) Date: Feb. 1, 2005

(87) PCT Pub. No.: WO2004/031885

PCT Pub. Date: Apr. 15, 2004

(65) Prior Publication Data

US 2005/0175228 A1    Aug. 11, 2005

Related U.S. Application Data

(60) Provisional application No. 60/399,727, filed on Aug. 1, 2002.

(51) Int. Cl.
*G06K 9/00* (2006.01)
(52) U.S. Cl. .................................................. 382/128
(58) Field of Classification Search ................. 382/128, 382/129, 262, 274, 275, 305
See application file for complete search history.

(56) References Cited

U.S. PATENT DOCUMENTS 7,099,502 B2 *    8/2006    Shams et al. ................. 382/129

(Continued)

FOREIGN PATENT DOCUMENTS

WO    WO 02/099071    12/2002

OTHER PUBLICATIONS

Bolstad, Ben, "Probe Level Quantile Normalization of High Density Oligonucleotide Array Data", Unpublished manuscript from www.stat.berkeley.edu/~bolstad, (2001).

(Continued)

*Primary Examiner*—Tom Y Lu
(74) *Attorney, Agent, or Firm*—Procopio, Cory, Hargreaves & Savitch, LLP

(57) ABSTRACT

An automated system and method are provided for analyzing gene expression data obtained from a plurality of microarrays having mismatch (MM) probe pairs and perfect match (PM) probe pairs. Image data for a plurality of scanned microarrays is stored in a database along with a set of microarray parameters which includes one or more image processing metrics for quality control of the microarray and a pass/fail status of the microarray as determined by these metrics. The user can search the database records according to one or more microarray parameters. The image processing metrics include algorithms for removing local background effects from the probe measurements by determining a model for estimated background using PM probe values. Other image processing metrics utilize a modified Robust Multi-array Averaging (RMA) applied to PM probes to assign weights to probes for determining overall quality of a microarray.

26 Claims, 16 Drawing Sheets

U.S. PATENT DOCUMENTS

| | | | |
|---|---|---|---|
| 7,398,171 B2 * | 7/2008 | Woo et al. | 702/82 |
| 2002/0110267 A1 | 8/2002 | Brown et al. | |
| 2003/0028501 A1 | 2/2003 | Balaban et al. | |
| 2003/0093227 A1 | 5/2003 | Stoughton et al. | |
| 2003/0099973 A1 | 5/2003 | Wang et al. | |
| 2003/0124589 A1 | 7/2003 | Piper | |
| 2003/0171876 A1 | 9/2003 | Markowitz et al. | |
| 2004/0019466 A1 | 1/2004 | Minor et al. | |

OTHER PUBLICATIONS

Bolstad, B.M., "Comparing the effects of background, normalization and summarization on gene expression estimates", Unpublished manuscript from www.stat.berkeley.edu/~bolstad, (2002).

Holder, Daniel et al., "Statistical Analysis of High Density Oligonucleotide Arrays: A *Safer* Approach" http://stat-www.berkeley.edu/users/terry/zarray/affy/GL_Workshop/genelogic2001.html, (2001).

Irizarry, Rafael A. et al. "Exploration, Normalization, and Summaries of High Density Oligonucleotide Array Probe Level Data", (2003) *Biostatistics* 4:249-264.

Lauren, Peter D., "Algorithm to Model Gene Expression on Affymetrix Chips Without the Use of MM Cells" *IEEE Trans. Nanobioscience*, Sep. 2003; 2(3):163-170.

Li, Cheng et al. "Model-based analysis of oligonucleotide arrays: Expression index computation and outlier detection",(2001) *PNAS* Jan. 2, 2001, vol. 98(1):31-36.

Affymetrix "Statistical Algorithms Description Document" © 2002 Affymetrix, Inc.

* cited by examiner

Image Processing Workflow

*FIG. 3*

| Site | Chip | ChipType | Tissue Type | IP Fail Count | IP Fail Description | Intensity All | Intens/BG | Image 5% |
|---|---|---|---|---|---|---|---|---|
| A | 1 | RG_U34A | LIVER, NOS | 2 | All, Artifacts, Uneven | 391 | 5.446 | 72 |
| A | 2 | RG_U34A | LIVER, NOS | 3 | All, Artifacts, Uneven | 463 | 6.88 | 67 |
| A | 3 | RG_U34A | LIVER, NOS | 2 | All, Artifacts, Uneven | 529 | 7.317 | 72 |
| A | 4 | RG_U34A | LIVER, NOS | 1 | All | 365 | 5.105 | 72 |
| A | 5 | RG_U34A | LIVER, NOS | 1 | All | 556 | 6.864 | 81 |
| A | 6 | RG_U34A | LIVER, NOS | 1 | All | 469 | 7.528 | 62 |
| A | 7 | RG_U34A | LIVER, NOS | 2 | All, Artifacts, Uneven | 469 | 6.312 | 74 |
| A | 8 | RG_U34A | LIVER, NOS | 2 | All, Artifacts, Uneven | 551 | 8.636 | 64 |
| A | 9 | RG_U34A | LIVER, NOS | 2 | All, Artifacts, Uneven | 369 | 6.119 | 60 |
| A | 10 | RG_U34A | LIVER, NOS | 2 | All, Artifacts, Uneven | 453 | 7.906 | 57 |
| A | 11 | RG_U34A | LIVER, NOS | 1 | All | 337 | 4.849 | 70 |
| A | 12 | RG_U34A | LIVER, NOS | 2 | All, Artifacts, Uneven | 362 | 5.3 | 68 |
| A | 13 | RG_U34A | LIVER, NOS | 1 | All | 333 | 4.69 | 71 |
| A | 14 | RG_U34A | LIVER, NOS | 5 | All, Artifacts, Grid, Uneven | 667 | 9.038 | 74 |
| A | 15 | RG_U34A | LIVER, NOS | 2 | All, Artifacts, Uneven | 321 | 4.735 | 68 |
| B | 1 | RG_U34A | LIVER, NOS | 0 | | 315 | 6.389 | 49 |
| B | 2 | RG_U34A | LIVER, NOS | 0 | | 295 | 4.836 | 61 |
| B | 3 | RG_U34A | LIVER, NOS | 0 | | 315 | 5.526 | 57 |
| B | 4 | RG_U34A | LIVER, NOS | 0 | | 306 | 5.741 | 53 |
| B | 5 | RG_U34A | LIVER, NOS | 2 | All, Haze Band | 294 | 5.043 | 58 |
| B | 6 | RG_U34A | LIVER, NOS | 0 | | 305 | 5.865 | 52 |
| B | 7 | RG_U34A | LIVER, NOS | 2 | Artifacts, Uneven | 419 | 6.135 | 68 |
| B | 8 | RG_U34A | LIVER, NOS | 1 | Artifacts, Uneven | 373 | 6.602 | 57 |
| B | 9 | RG_U34A | LIVER, NOS | 11 | Artifacts, Haze Band, Intensity, Uneven | 1294 | 12.686 | 102 |
| B | 10 | RG_U34A | LIVER, NOS | 2 | All, Artifacts, Uneven | 508 | 6.773 | 75 |
| B | 11 | RG_U34A | LIVER, NOS | 1 | All | 294 | 5.845 | 50 |
| B | 12 | RG_U34A | LIVER, NOS | 2 | Artifacts, Uneven | 399 | 7.087 | 56 |
| B | 13 | RG_U34A | LIVER, NOS | 1 | Artifacts, Uneven | 417 | 6.915 | 60 |
| B | 14 | RG_U34A | LIVER, NOS | 0 | | 296 | 6.004 | 49 |
| B | 15 | RG_U34A | LIVER, NOS | 1 | All | 208 | 3.014 | 69 |

*FIG. 4A*

| Negative PM-MM | Mean AvgDiff | Raw 5'/3' GapDH | Raw 5'/3' B-Actin | Intensity Spikeins | Intensity OligoB2 | Li/Wong Outliers | Saturation Count | Vert 10% peak/med | Spikeln Intercept |
|---|---|---|---|---|---|---|---|---|---|
| 46327 | 118 | 0.935 | 0.685 | 156 | 11733 | 2619 | 0 | 1.095 | 3.597 |
| 46522 | 153 | 0.847 | 0.721 | 238 | 10182 | 2690 | 0 | 1.105 | 4.146 |
| 45037 | 194 | 0.942 | 0.804 | 324 | 10683 | 2666 | 0 | 1.075 | 4.242 |
| 47464 | 107 | 0.95 | 0.729 | 188 | 11770 | 2681 | 0 | 1.086 | 4.143 |
| 46077 | 182 | 0.829 | 0.741 | 271 | 10916 | 2676 | 0 | 1.085 | 4.23 |
| 45626 | 164 | 0.897 | 0.684 | 427 | 11569 | 2856 | 2 | 1.073 | 4.934 |
| 45838 | 170 | 0.889 | 0.792 | 298 | 7980 | 2687 | 0 | 1.078 | 3.88 |
| 44793 | 195 | 0.873 | 0.664 | 197 | 10089 | 2823 | 0 | 1.068 | 4.244 |
| 45615 | 123 | 0.965 | 0.626 | 286 | 9582 | 2615 | 0 | 1.054 | 5.043 |
| 44523 | 175 | 0.953 | 0.734 | 243 | 9574 | 2900 | 0 | 1.094 | 3.806 |
| 47193 | 107 | 1.016 | 0.687 | 214 | 11018 | 2758 | 0 | 1.065 | 4.309 |
| 47243 | 101 | 0.909 | 0.699 | 188 | 12237 | 2620 | 0 | 1.084 | 3.113 |
| 46881 | 105 | 0.904 | 0.75 | 187 | 10477 | 2582 | 0 | 1.08 | 3.368 |
| 44376 | 270 | 0.935 | 0.75 | 331 | 11284 | 2646 | 0 | 1.108 | 4.146 |
| 47765 | 85 | 0.944 | 0.7 | 178 | 11579 | 2574 | 0 | 1.127 | 3.758 |
| 46492 | 110 | 0.866 | 0.692 | 61 | 2906 | 2598 | 0 | 1.089 | 4.157 |
| 47925 | 94 | 0.901 | 0.711 | 64 | 2652 | 2349 | 0 | 1.088 | 4.214 |
| 47385 | 103 | 0.852 | 0.695 | 70 | 3113 | 2436 | 0 | 1.166 | 4.345 |
| 46434 | 102 | 0.862 | 0.689 | 57 | 2332 | 2533 | 0 | 1.149 | 4.1 |
| 47087 | 85 | 0.88 | 0.723 | 65 | 2629 | 2421 | 0 | 1.265 | 4.269 |
| 45981 | 98 | 0.861 | 0.725 | 73 | 2835 | 2511 | 0 | 1.152 | 4.34 |
| 47663 | 130 | 0.854 | 0.747 | 75 | 3241 | 2384 | 0 | 1.064 | 4.362 |
| 47533 | 111 | 0.845 | 0.746 | 88 | 2946 | 2373 | 0 | 1.058 | 4.623 |
| 51529 | 266 | 1.012 | 0.581 | 104 | 4521 | 1761 | 1 | 1.357 | 4.969 |
| 46733 | 174 | 0.906 | 0.73 | 108 | 4516 | 2508 | 0 | 1.098 | 4.693 |
| 46909 | 90 | 0.897 | 0.666 | 54 | 2432 | 2411 | 0 | 1.13 | 4.056 |
| 46670 | 128 | 0.813 | 0.717 | 72 | 3478 | 2483 | 0 | 1.071 | 4.383 |
| 47504 | 118 | 0.866 | 0.659 | 90 | 4211 | 2347 | 0 | 1.072 | 4.68 |
| 46688 | 94 | 0.837 | 0.676 | 75 | 2793 | 2562 | 1 | 1.12 | 4.44 |
| 49044 | 62 | 0.681 | 0.693 | 48 | 3336 | 2404 | 0 | 1.046 | 3.894 |

*FIG. 4B*

| Spikeln Slope | Vert Outlier Var | Horiz Outlier Var | Top Outlier Edge Ratio | Bottom Outlier Edge Ratio | Left Outlier Edge Ratio | Right Outlier Edge Ratio | 25% Top Edge Ratio | 25% Bottom Edge Ratio | 25% Left Edge Ratio |
|---|---|---|---|---|---|---|---|---|---|
| 0.653 | 22.646 | 13.817 | 0.836 | 0.913 | 0.801 | 0.946 | 1.182 | 0.947 | 1 |
| 0.64 | 29.924 | 17.055 | 0.764 | 0.897 | 1.079 | 0.928 | 1.197 | 0.95 | 1.022 |
| 0.707 | 24.722 | 18.077 | 0.9 | 0.917 | 1.139 | 0.878 | 1.18 | 0.948 | 1.062 |
| 0.497 | 28.449 | 16.471 | 0.908 | 0.824 | 0.819 | 0.938 | 1.137 | 0.981 | 1.046 |
| 0.699 | 28.735 | 23.511 | 0.81 | 0.86 | 1.15 | 0.864 | 1.131 | 0.956 | 1.043 |
| 0.666 | 30.882 | 17.744 | 0.767 | 0.908 | 0.952 | 0.858 | 1.138 | 0.947 | 1.025 |
| 0.81 | 16.837 | 19.078 | 0.847 | 0.963 | 1.012 | 0.995 | 1.167 | 0.959 | 1.016 |
| 0.716 | 30.097 | 23.347 | 0.774 | 0.94 | 0.989 | 0.957 | 1.223 | 0.966 | 1.047 |
| 0.424 | 29.957 | 15.748 | 0.886 | 0.98 | 0.883 | 0.797 | 1.092 | 1.029 | 1.014 |
| 0.779 | 29.609 | 18.137 | 0.811 | 0.811 | 1.083 | 0.95 | 1.207 | 0.976 | 1.064 |
| 0.501 | 24.843 | 19.022 | 0.84 | 0.938 | 0.888 | 0.92 | 1.156 | 0.968 | 1.014 |
| 0.851 | 24.225 | 16.097 | 0.852 | 0.876 | 0.759 | 0.911 | 1.155 | 0.969 | 0.988 |
| 0.807 | 24.343 | 8.665 | 0.841 | 0.78 | 0.943 | 1.03 | 1.145 | 0.979 | 1.02 |
| 0.823 | 25.686 | 23.463 | 0.83 | 0.83 | 1.19 | 0.743 | 1.282 | 0.962 | 1.101 |
| 0.641 | 23.967 | 14.159 | 0.858 | 0.875 | 0.902 | 0.972 | 1.199 | 0.927 | 1.038 |
| 0.941 | 24.777 | 22.401 | 0.802 | 0.802 | 0.96 | 0.908 | 1.14 | 0.976 | 0.953 |
| 0.93 | 21.79 | 17.26 | 0.837 | 0.876 | 1.066 | 0.883 | 1.076 | 1.013 | 0.991 |
| 0.91 | 23.558 | 16.515 | 0.764 | 0.949 | 0.994 | 0.873 | 1.077 | 1.023 | 0.977 |
| 0.93 | 23.148 | 12.457 | 0.779 | 0.832 | 1.07 | 0.886 | 1.068 | 1.004 | 1.022 |
| 0.889 | 18.967 | 17.122 | 0.838 | 0.996 | 1.113 | 0.919 | 1.034 | 0.972 | 1.028 |
| 0.932 | 25.84 | 21.033 | 0.786 | 0.849 | 1.052 | 1.008 | 1.106 | 0.998 | 1.02 |
| 0.92 | 19.927 | 17.095 | 0.696 | 0.912 | 0.936 | 0.889 | 1.058 | 1.022 | 0.898 |
| 0.863 | 25.018 | 18.476 | 0.823 | 0.927 | 1.073 | 1.016 | 1.091 | 1.012 | 0.947 |
| 0.764 | 19.74 | 9.226 | 0.943 | 1.08 | 1.144 | 0.979 | 0.742 | 0.568 | 0.885 |
| 0.957 | 20.442 | 18.247 | 0.887 | 0.923 | 0.993 | 0.905 | 1.153 | 1.05 | 1.05 |
| 0.915 | 15.961 | 12.333 | 0.813 | 0.86 | 1.015 | 0.923 | 1.065 | 0.991 | 1.018 |
| 0.899 | 26.67 | 18.798 | 0.828 | 0.864 | 0.981 | 0.918 | 1.102 | 1.017 | 0.936 |
| 0.834 | 18.036 | 18.717 | 0.874 | 0.96 | 1.019 | 0.952 | 1.114 | 1.012 | 0.955 |
| 0.887 | 25.912 | 17.238 | 0.746 | 0.895 | 1.051 | 0.955 | 1.148 | 0.993 | 1.037 |
| 0.92 | 15.16 | 10.043 | 0.935 | 0.935 | 1.141 | 1.022 | 1.058 | 0.988 | 1.02 |

*FIG. 4C*

| 25% Right Edge Ratio | 75% Top Edge Ratio | 75% Bottom Edge Ratio | 75% Left Edge Ratio | 75% Right Edge Ratio | Horiz 25% Max/Min | Vert 25% Max/Min | Horiz 75% Max/Min | Vert 75% Max/Min | Affy Outliers |
|---|---|---|---|---|---|---|---|---|---|
| 1.082 | 1.494 | 0.888 | 0.981 | 1.16 | 1.197 | 1.475 | 1.648 | 2.554 | 26 |
| 1.108 | 1.531 | 0.904 | 1.019 | 1.25 | 1.195 | 1.535 | 1.645 | 2.69 | 18 |
| 1.055 | 1.541 | 0.855 | 1.185 | 0.967 | 1.146 | 1.533 | 1.365 | 2.802 | 10 |
| 1.084 | 1.374 | 0.944 | 1.042 | 1.185 | 1.146 | 1.375 | 1.522 | 2.287 | 46 |
| 1.057 | 1.413 | 0.9 | 1.112 | 1.093 | 1.143 | 1.445 | 1.476 | 2.46 | 6 |
| 1.078 | 1.441 | 0.875 | 1.078 | 1.105 | 1.203 | 1.428 | 1.526 | 2.541 | 45 |
| 1.091 | 1.486 | 0.93 | 0.999 | 1.202 | 1.179 | 1.517 | 1.639 | 2.651 | 18 |
| 1.102 | 1.613 | 0.909 | 1.088 | 1.201 | 1.192 | 1.629 | 1.583 | 3.077 | 40 |
| 1.128 | 1.309 | 1.043 | 1.051 | 1.071 | 1.214 | 1.348 | 1.439 | 2.507 | 63 |
| 1.02 | 1.556 | 0.895 | 1.105 | 1.099 | 1.139 | 1.546 | 1.478 | 2.946 | 194 |
| 1.108 | 1.556 | 0.884 | 1.031 | 1.174 | 1.187 | 1.359 | 1.541 | 2.607 | 111 |
| 1.115 | 1.476 | 0.895 | 0.963 | 1.136 | 1.227 | 1.373 | 1.668 | 2.477 | 118 |
| 1.068 | 1.402 | 0.929 | 1.034 | 1.118 | 1.122 | 1.35 | 1.489 | 2.347 | 112 |
| 1.018 | 1.828 | 0.863 | 1.276 | 0.902 | 1.211 | 1.69 | 1.598 | 3.552 | 27 |
| 1.079 | 1.612 | 0.783 | 1.09 | 1.139 | 1.146 | 1.456 | 1.453 | 2.711 | 28 |
| 1.01 | 1.41 | 0.941 | 0.981 | 1.063 | 1.176 | 1.363 | 1.447 | 2.318 | 50 |
| 1.003 | 1.413 | 0.961 | 1.012 | 1.058 | 1.111 | 1.308 | 1.328 | 2.355 | 28 |
| 1.03 | 1.437 | 0.961 | 1.057 | 1.034 | 1.135 | 1.385 | 1.364 | 2.521 | 46 |
| 0.981 | 1.406 | 0.95 | 1.049 | 1.001 | 1.109 | 1.378 | 1.316 | 2.372 | 18 |
| 1.002 | 1.333 | 0.965 | 1.169 | 1.017 | 1.115 | 1.445 | 1.336 | 2.219 | 65 |
| 1.024 | 1.442 | 0.941 | 1.035 | 1.125 | 1.118 | 1.42 | 1.447 | 2.554 | 38 |
| 1.015 | 1.305 | 0.947 | 0.881 | 1.01 | 1.237 | 1.419 | 1.539 | 2.317 | 23 |
| 0.928 | 1.395 | 0.952 | 0.922 | 0.861 | 1.188 | 1.41 | 1.434 | 2.478 | 77 |
| 1.354 | 0.999 | 0.627 | 0.91 | 1.321 | 2.146 | 2.741 | 2.074 | 2.323 | 575 |
| 1.014 | 1.477 | 0.979 | 1.071 | 1.054 | 1.161 | 1.529 | 1.423 | 2.745 | 104 |
| 1.005 | 1.33 | 0.905 | 1.087 | 0.987 | 1.121 | 1.38 | 1.346 | 2.274 | 61 |
| 0.947 | 1.42 | 0.936 | 0.873 | 0.926 | 1.183 | 1.408 | 1.529 | 2.557 | 33 |
| 0.955 | 1.37 | 0.928 | 0.933 | 0.93 | 1.189 | 1.463 | 1.474 | 2.403 | 55 |
| 1 | 1.465 | 0.924 | 1.02 | 1.075 | 1.116 | 1.421 | 1.368 | 2.58 | 20 |
| 1.032 | 1.444 | 1.007 | 1.106 | 1.054 | 1.087 | 1.148 | 1.38 | 2.26 | 133 |

*FIG. 4D*

| log(Intens)/ log(BG) | SpikeIn R-Squared | Lot Num | Scanner | Fluidics | Fluid Sta | Fluid Pos |
|---|---|---|---|---|---|---|
| Not Available | Not Available | Not Available | Not Available | Not Available | Not Available | Not Available |
| Not Available | Not Available | Not Available | Not Available | Not Available | Not Available | Not Available |
| Not Available | Not Available | Not Available | Not Available | Not Available | Not Available | Not Available |
| Not Available | Not Available | Not Available | Not Available | Not Available | Not Available | Not Available |
| Not Available | Not Available | Not Available | Not Available | Not Available | Not Available | Not Available |
| Not Available | Not Available | Not Available | Not Available | Not Available | Not Available | Not Available |
| Not Available | Not Available | Not Available | Not Available | Not Available | Not Available | Not Available |
| Not Available | Not Available | Not Available | Not Available | Not Available | Not Available | Not Available |
| Not Available | Not Available | Not Available | Not Available | Not Available | Not Available | Not Available |
| Not Available | Not Available | Not Available | Not Available | Not Available | Not Available | Not Available |
| Not Available | Not Available | Not Available | Not Available | Not Available | Not Available | Not Available |
| Not Available | Not Available | Not Available | Not Available | Not Available | Not Available | Not Available |
| Not Available | Not Available | Not Available | Not Available | Not Available | Not Available | Not Available |
| Not Available | Not Available | Not Available | Not Available | Not Available | Not Available | Not Available |
| Not Available | Not Available | Not Available | Not Available | Not Available | Not Available | Not Available |
| 1.476 | 0.968 | 2001343 | scanner13 | fluidics03 | 5 | 1 |
| 1.383 | 0.973 | 2001343 | scanner02 | fluidics03 | 4 | 3 |
| 1.423 | 0.976 | 2001343 | scanner09 | fluidics03 | 3 | 2 |
| 1.44 | 0.972 | 2001343 | scanner14 | fluidics03 | 1 | 1 |
| 1.398 | 0.965 | 2001343 | scanner01 | fluidics03 | 1 | 4 |
| 1.448 | 0.971 | 2001343 | scanner02 | fluidics03 | 2 | 2 |
| 1.429 | 0.965 | 2001343 | scanner15 | fluidics04 | 3 | 1 |
| 1.468 | 0.976 | 2000426 | scanner15 | fluidics03 | 8 | 3 |
| 1.549 | 0.971 | 2000426 | scanner04 | fluidics04 | 1 | 3 |
| 1.443 | 0.962 | 2000426 | scanner05 | fluidics04 | 4 | 1 |
| 1.451 | 0.961 | 2000426 | scanner14 | fluidics04 | 2 | 2 |
| 1.486 | 0.976 | 2000426 | scanner15 | fluidics03 | 6 | 3 |
| 1.472 | 0.973 | 2000426 | scanner15 | fluidics03 | 7 | 4 |
| 1.46 | 0.978 | 2000426 | scanner02 | fluidics03 | 8 | 1 |
| 1.261 | 0.929 | 2000426 | scanner05 | fluidics03 | 5 | 3 |

*FIG. 4E*

| IP Fail Flags |
|---|
| 00000010 00000000 00000000 00100000 |
| 00000010 10000000 00000000 00100000 |
| 00000010 00000000 00000000 00100000 |
| 00000000 00000000 00000000 00100000 |
| 00000000 00000000 00000000 00100000 |
| 00000000 00000000 00000000 00100000 |
| 00000010 00000000 00000000 00100000 |
| 00000010 00000000 00000000 00100000 |
| 00000000 00001000 00000000 00100000 |
| 00000010 00000000 00000000 00100000 |
| 00000000 00000000 00000000 00100000 |
| 00000000 00001000 00000000 00100000 |
| 00000000 00000000 00000000 00100000 |
| 00000010 01010000 01000000 00100000 |
| 00000000 00100000 00000000 00100000 |
| 00000000 00000000 00000000 00000000 |
| 00000000 00000000 00000000 00000000 |
| 00000000 00000000 00000000 00000000 |
| 00000000 00000000 00000000 00000000 |
| 00000000 00000000 00000000 01100000 |
| 00000000 00000000 00000000 00000000 |
| 00000000 01000100 00000000 00000000 |
| 00000000 00000100 00000000 00000000 |
| 00000111 10101111 00000000 01000100 |
| 00000010 00000000 00000000 00100000 |
| 00000000 00000000 00000000 00100000 |
| 00000000 01000100 00000000 00000000 |
| 00000010 00000000 00000000 00000000 |
| 00000000 00000000 00000000 00000000 |
| 00000000 00000000 00000000 00100000 |

*FIG. 4F*

| Fields | DESCRIPTION |
|---|---|
| ID | Sequence (Primary Key) |
| CHIPID | Not used |
| EXPERIMENTNA | Link to chip table |
| PROCESSID | From CV_PROCESS |
| PERSON | User or Application |
| DATETIME | Timestamp |
| HISTORY | CURRENT or HISTORY |
| PROBLEMID | From CV_PROBLEM (>0 if |
| FILENAME | Filename from Analysis or |

*FIG. 5*

| ID | DESCRIPTI |
|---|---|
| ANALYSIS | Analysis |
| VALIDATE | Validate |
| IMAGEPRO | Image |
| VQC | Visual QC |
| MASK | Mask |
| VALIDCHP | Validate |
| IMPORT | Import |
| PUBLISH | Publish |
| ARCHIVE | Archive |

*FIG. 6*

| ID | DESCRIPTION |
|---|---|
| 0 | ok |
| 1 | DAT file not found after scan |
| 2 | CEL file not found after scan |
| 3 | DAT file created without DB entry |
| 4 | CHP file is not found |
| 5 | CEL file has been modified or |
| 6 | Analyzed with incorrect parameters |
| 7 | Analyzed without visual QC |
| 8 | CEL file created without DB entry |
| 9 | CHP file created without DB entry |
| 10 | CEL file is older than DAT file |
| 11 | CHP file is older than CEL file |
| 12 | Failed Visual QC |
| 13 | Failed Image Processing |

*FIG. 7*

| Fields | DESCRIPTION |
|---|---|
| CHIPID | PK |
| EXPERIMENTNAM | From Affy |
| PERSON | QCUser |
| PROBEARRAYTY | From Affy |
| COMMENTS | |
| QCDATE | Timestamp |
| LOTNUMBER | From Affy |
| PASSFAIL | Set by vqc user |
| DATESTAMP | Current date |
| FAILREASON | Reason chip failed QC – (no longer same as defect reason) |
| NEEDSMASK | Flag indicating image needs to be masked (set by vqc user from QC |
| MASKED | Flag indicating has been masked ('Y') or not (blank) Set from Qualms |
| IP_FAILFLAGS | 25 flag bits. 1=corresponding metric is out of range (failed) |
| IP_FAILDESCRIPT | Description of defects implied by failed metrics |
| IP_LIMITSVER | Version number of limits used to compute IP_FAILFLAGS |
| 32 IP Metric columns | IP_INTENSALL, IP_INTENSSPIKE*, IP_INTENSOLIGOB2*, IP_OUTLIERS, IP_SATUR, IP_SPIKEINR2, IP_VERT10, IP_SPIKEINICPT*, IP_SPIKEINSLOPE*, IP_NEGATIVEPP, IP_VERTOUTVAR, IP_HOROUTVAR, IP_TOPOUTEDGE, IP_BOTTOMOUTEDGE, IP_LEFTOUTEDGE, IP_RIGHTOUTEDGE, IP_TOPEDGE25, IP_BOTTOMEDGE25, IP_LEFTEDGE25, IP_RIGHTEDGE25, IP_TOPEDGE75, IP_BOTTOMEDGE75, IP_LEFTEDGE75, IP_RIGHTEDGE75, IP_HOR25MINMAX, IP_VERT25MINMAX, IP_HOR75MINMAX, IP_VERT75MINMAX, IP_INTENSE5TH, IP_53GAPDH*, IP_53BACTIN*, IP_MEANAVDIFF* <br> *= no limits for these metrics |

*FIG. 8*

| Fields | DESCRIPTION |
|---|---|
| DEFECTID | Sequence (Primary Key) |
| OLDDEFECTDESCR | For historic reasons – no longer used |
| CLASS | Defect type |
| IMAGE | Not used |
| CHIPID | FK, Link to ChipDefects PK |
| QUADRANT | Not used |
| DEFECTDESCRIPTI | New Description, linked to CV_FAILREASON |

*FIG. 9*

| Fields | DESCRIPTION |
|---|---|
| DEFECTID | Sequence (Primary Key) |
| SHAPE | 0=rectangle, 1=ellipse |
| IMAGE_LEFT | Defect location in image coordinates |
| IMAGE_RIGHT | |
| IMAGE_TOP | |
| IMAGE_BOTTOM | |
| GRID_LEFT | Defect location in cel file (grid) coordinates |
| GRID_RIGHT | |
| GRID_TOP | |
| GRID_BOTTOM | |

*FIG. 10*

| REASON |
|---|
| Bright Locally |
| Bright Overall |
| Cracked |
| Crop Circle |
| Dim Locally |
| Dim Overall |
| Haze Band |
| Haze |
| High Background |
| Incorrect Probearray |
| Incorrect Scanner Setting |
| No Sample |
| Other |
| Scanner Failure |
| Snow |

*FIG. 11*

| Column | Table | DESCRIPTION |
|---|---|---|
| LOT RUN ID | AFFX PHYSICAL AR | Lot Number |
| PROBE ARRAY NA | AFFX PHYSICAL AR | Chip Type – used to update ProbeArrayType in Chip |
| EXP COMMENT | AFFX ARRAY EXPER | Scanner setting (High/Low) |
| PROJECT NAME | AFFX SAMPLE | Project name |
| SCANDATE | CHIP HYB SCAN INF | Scan Date |
| SCANNER | CHIP HYB SCAN INF | Scanner Name |
| FLUIDICS | CHIP HYB SCAN INF | Fluidics Name |
| STATION | CHIP HYB SCAN INF | Fluidics Station |
| POSITION | CHIP HYB SCAN INF | Fluidics Position |

*FIG. 12*

METHOD AND SYSTEM FOR MANAGING AND QUERYING GENE EXPRESSION DATA ACCORDING TO QUALITY

RELATED APPLICATIONS

This application claims benefit of the priority of U.S. Provisional Patent Application No. 60/399,727 filed Aug. 1, 2002, the disclosure of which is incorporated herein by reference in its entirety.

FIELD OF THE INVENTION

The present invention relates generally to a method and system for managing the quality control process in the analysis of gene expression data from DNA probe arrays. More particularly, but not by way of limitation, the present invention relates to a centralized application involving enhanced functionality, permitting users to query on numerous chip parameters, and display and arrange results on a flexible grid.

BACKGROUND OF THE INVENTION

To understand gene function, it is helpful to know when and where it is expressed, and under what circumstances the expression level is affected. Beyond questions of individual gene function are also questions concerning functional pathways and how cellular components work together to regulate and carry out cellular processes. Addressing these questions requires the quantitative monitoring of the expression levels of very large number of genes repeatedly, routinely and reproducibly, while starting with a reasonable number of cells from a variety of sources and under the influences of genetic, biochemical and chemical perturbations.

In order to maximize confidence in gene fragment estimates using oligonucleotide microarrays such as the Affymetrix GeneChip® microarrays, it is necessary to identify arrays that are contaminated with artifacts not representative of expression levels of the fragments of interest. Obtaining reliable estimates of gene expression from raw measurements on microarrays presents several problems due to background contributions, non-specific probe response, possible variation in probe sensitivities and possible non-linear responses of the probes to transcript concentration. While it is recognized that quality control measures should be implemented in generating gene expression data, existing quality control techniques employ limited functionality. These processes lack effective centralized applications to flexibly display search results, process large amounts of data, illuminate the differences between data sources, and automatically identify and address problems.

In many prior art techniques, quality control (QC) has been based upon visual evaluations by a live inspector. A book of standard defective images is assembled and used for comparison for the image under inspection. Basically, the inspector would look for probe level deviations from the expected behavior, then total the number of potentially defective probes across the entire chip to determine whether to pass or fail that chip. Such manual inspection procedures raise a number of problems including, but not limited to: 1) the large number of operator hours are required; 2) the nature of the inspection makes it highly subjective; 3) there can be a continuum between gross artifacts and no artifacts which can affect an operator's decision to flag an array; and 4) certain artifacts such as grid misalignment are difficult to detect visually.

One of the early approaches for instrument-based detection of these defects involved the use of thresholds for brightness and dimness, which was one of the simpler tests. However, some of the images can be very uneven in the background and non-uniform such that the overall signal intensity alone may not be a good test. As a result, other comparisons have been utilized, including evaluation of lines, ratios and profiles.

One of the more critical metrics in assessing a genome chip is the overall chip brightness involving an estimate of the background noise on the chip. The overall chip brightness provides a basis for an automatic pass or fail.

A widely used quality metric for gene expression data involves the use of mismatch (MM) control probe pairs that are identical to their perfect match (PM) partners except for a single base difference in a central position. The MM probe pairs act as specificity controls that allow the direct subtraction of both background and cross-hybridization signals, and allow discrimination between "real" signals and those resulting from non-specific or semi-specific hybridization. (Hybridization of the intended RNA molecules should produce a larger signal for the PM probes than for the MM probes, resulting in patterns that are highly unlikely to occur by chance. The pattern recognition rules are codified in analysis software.) In the presence of even low concentrations of RNA, hybridization of the PM/MM pairs produces recognizable and quantitative fluorescent patterns. The strength of these patterns directly relates to the concentration of the RNA molecules in the complex sample. Thus, PM/MM probe sets should permit the determination of whether a signal is generated by hybridization of the intended RNA molecule. However, some research has shown that a certain percentage of the MM probes are consistently brighter than their corresponding PM probes, and that there is often intensity variation between adjacent MM probes, suggesting that the response of the MM probes may be too transcript-specific to accurately measure background.

Using the PM/MM probe sets, a method has been described in which the expression levels of gene fragments may be modeled on an Affymetrix® GeneChip® microarray according to the following formula:

$$y_{ij} = PM_{ij} - MM_{ij} = \theta_i \phi_j + \epsilon_{ij}, \quad (1)$$

where i is the index of the array, j is the index of the probe pair for the fragment under consideration, $y_{ij}$ denotes the probe-pair difference, PM is the signal intensity, or value, of the PM probe and MM is the signal intensity, or value, of the MM probe. $\theta_i$ is the model-based expression index (MBEI) of the fragment in array i and $\phi_j$ is the derivative of the response of the $j^{th}$ probe for the fragment with respect to the MBEI. $\phi_j$ is also referred to as the probe sensitivity index ("PSI") of probe j. $\epsilon_{ij}$ is the error term. Outliers identified according to this model are sometimes referred to as "Li-Wong outliers". (See Li, C. and Wong, W. H., "Model-based analysis of oligonucleotide arrays: Expression index computation and outlier detection", *PNAS* 98(1):31-36, 2001, which is incorporated herein by reference in its entirety.)

In view of the aforementioned problems with the MM probes, a different model for estimating gene expression levels using only PM probes was proposed by Li and Wong ("Model-based analysis of oligonucleotide arrays: model validation, design issues and standard error application", *Genome Biology* 2(8): research 0032.1-0032.11, 2001, which is incorporated herein by reference in its entirety.) That model is $$PM_{ij} = \nu_j + \theta_i \phi'_j, \quad (2)$$

where $v_j$ is the baseline response of probe pair j to non-specific hybridization, $\theta_i$ is the MBEI of the fragment in array i, and $\phi_j'$ is the sensitivity of the PM probe or probe pair j. The parameter estimates are obtained by iteratively fitting $\theta_i$ and $v_j$, $\phi_j'$, while treating the other set as known. This model does not take into account the background structure which may vary independently of individual probes. Such background variation may be the result of defects such as haze and localized artifacts. As a result, both Li-Wong models can be somewhat limited in their reliability and accuracy.

The above-described metrics are not merely used for chip quality control (QC), but may also be used for process validation and checking scanners, among other tests. If a process change does not affect the metrics, it is likely to not affect the quality. If it does affect the metrics, then there may be a corresponding impact on the quality of the expression data.

Accordingly, the need exists for an improved method and system to reliably determine the quality of gene expression data obtained using microarrays and to exclude data that is unreliable, whether the poor quality results from defects on the microarrays themselves or from instrument-based errors. The present invention is directed to such a system and method.

SUMMARY OF THE INVENTION

It is an object of the present invention to provide a centralized application for viewing, masking and pass/failing DNA probe microarrays, or "chips", making use of the image processing (IP) metrics and limits.

It is another object of the present invention to incorporate automated image processing metrics and limits into the QC process to provide quantitative measurements which can be used to establish the pass/fail status of a chip.

Still another object of the present invention is to provide a history and current status of experiments as they pass through the QC process, including problem detection and resolution.

Yet another object of the present invention is to provide methods for global and local evaluation within a single microarray and for multiple array evaluation for purposes of quality control.

In an exemplary embodiment, an automated system and method are provided for analyzing gene expression data obtained from a plurality of chips having mismatch (MM) probe pairs and perfect match (PM) probe pairs. Image data for a plurality of scanned microarrays is stored in a database along with a set of chip parameters which includes one or more image processing metrics for quality control of the chip and a pass/fail status of the microarray as determined by these metrics. The user can search the database records according to one or more chip parameters. The image processing metrics include algorithms for removing local background effects from the probe measurements by determining a model for estimated background using PM probe values. Other image processing metrics utilize a modified Robust Multi-array Averaging (RMA) applied to PM probes to assign weights to probes for determining overall quality of a microarray.

According to the present invention, a centralized application is provided for viewing, masking and pass/failing chips, and making use of the Image Processing (IP) metrics and limits. One aspect of the invention is to provide an improved method and system for incorporating the automated IP metrics and limits into the Quality Control (QC) process in order to provide quantitative measurements which can be used to help establish the pass/fail status of a chip. Another aspect of the invention provides an improved method and system for providing a history and current status of experiments as they pass through the QC process, including problem detection and resolution.

In an exemplary embodiment, the QC process occurs between the time that chips are scanned and the time the resulting gene expression data are published, e.g., stored in a database. In one embodiment, scanning of the microarray generates a DAT image file. A grid is automatically placed over the DAT file to demarcate each probe cell, then the DAT file is analyzed. Following this analysis, a CEL file is generated containing probe intensity data associated with a position within an x, y coordinate field. The information for each file is recorded in a database, for example, the Affymetrix® ProcessDB database. Images are then visually inspected and assigned a "Pass" or "Fail" status. Approximately 5% of the passed images have defects that need to be masked. If more than about 5% of the area on a chip contains defects, the chip is failed. After Visual Quality Control ("VQC"), and masking, if necessary, a CHP file is generated by the "Analysis" process. The CHP file contains average intensity measurements for each gene or fragment on a chip. Following Analysis, the data are published.

In other embodiments, image processing is run on CEL files prior to visual QC in order to help evaluate image quality. Microarrays that fail most or all of the prescribed metrics can be automatically failed, thus by-passing visual inspection. Microarrays that fail one or more metrics are visually inspected by the QC operator, who can double check for defects based on the failed metrics. Microarrays may be masked to exclude small defects from an otherwise good chip. By selecting an appropriate set of metrics with sufficiently rigorous pass criteria, it may even be possible for microarrays that pass all of the prescribed metrics to by-pass visual inspection.

In further embodiments, in addition to visual QC and masking, several scripts are executed in the background as scheduled tasks. These scripts are used to move and copy files within the system and perform numerous validity and consistency checks on files and database tables. The scripts verify that a database record exists for each file and that files exist for each database record. The scripts also check file sizes, creation dates and owners. Analysis, publishing, and importing of data are all done through scheduled scripts using, for example, the Affymetrix® LIMS 3 API. Backup and archiving are also scheduled scripts.

In an exemplary embodiment, the present invention is a centralized application capable of tracking the processes as a chip moves from registration and scan to publish and beyond. This application permits users to view experiments, mask experiments if necessary, set pass/fail status and fail reason if fail, correct problems, view any of a number of chip parameters including IP (image processing) metrics and limits, query chip current status and/or history based on most of the preceding parameters, quickly reorder or hide columns, quickly sort multiple columns and print, or export all or part of the current display for further analysis, for example, using Microsoft Excel® or other third party software.

Other embodiments of the present invention include a lightweight, ActiveX® component image viewer (from Microsoft Corporation, Redmond, Wash.) where the metrics can be visualized more easily. The component image viewer provides additional capabilities including a stand-alone system which permits system users to send images and run metrics on the images, displaying the metrics and limit information in a grid, even if the chips are not part of any LIMS system.

A further embodiment of the present invention uses the actual gene expression values to determine if a chip should be passed or failed. Initially, the pass/fail status of historic chips is used to establish acceptable limits for the IP metrics. Metrics are calculated for a set of passed chips and a set of failed chips and significance tests are used to detect statistically significant differences. Limits can be set to include most of the passed chips while excluding most of the failed chips; however, the process of setting the limits themselves can become a significant issue in determining which metrics to use to define the limits.

In one aspect of the invention, a method is provided for analyzing gene expression data obtained from a plurality of microarrays having a plurality of probes, wherein the plurality of probes includes mismatch (M probe pairs having a mismatch value and perfect match (PM) probe pairs having a perfect match value. The method comprises the steps of: obtaining image data corresponding to scanned microarrays, the image data for each scanned microarray comprising an image corresponding to the scanned probe intensities, scan date, and at least one chip identifier; storing the image data for each scanned microarray in at least one database; applying an automated quality control process, comprising the steps of, in a processor, processing the image data by applying at least a portion of a plurality of image processing metrics comprising algorithms adapted to identify one or more defects selected from the group consisting of haze, bright artifacts, dim artifacts, crop circles, snow, snow, misalignment, grid misalignment, high background intensity, saturation, scratches, cracks; flagging any identified defects; assigning a pass/fail status to each microarray based upon identified defects, if any; storing the processed image data in the at least one database, the processed image data comprising the scanned probe intensities, the scan date, the at least one chip identifier, the pass/fail status, the applied image processing metrics, and the identified defects, if any; providing a user interface for searching the at least one database by selecting at least one chip parameter from the group consisting of scan date, the at least one chip identifier, the pass/fail status and the plurality of image processing metrics; and displaying the results of the search.

In another aspect of the invention, the quality metrics comprise a plurality of algorithms for detection of outliers resulting from commonly encountered defects. Among these quality metrics are algorithms for estimating background effects both locally, across a single chip and across multiple chips, allowing for probe data to be normalized to remove background effects.

In another aspect of the invention, an automated system is provided for analyzing gene expression data obtained from a plurality of chips having a plurality of probes, wherein the plurality of probes includes mismatch (MM) probe pairs having a mismatch value and perfect match (PM) probe pairs having a perfect match value. The system comprises: a database for storing image data for a plurality of scanned chips comprising an image corresponding to scanned probe intensities and a plurality of chip parameters corresponding to the scanned chip, wherein the chip parameters are selected from a group consisting of scan date, chip type, lot number, image processing metrics, and pass/fail status; a user interface for receiving a user query comprising at least one chip parameter and for displaying information responsive to the query; a processor for processing the image data for quality control by applying at least one of a plurality of image processing metrics adapted to identify defects selected from the group consisting of haze, bright artifacts, dim artifacts, crop circles, snow, snow, misalignment, grid misalignment, high background intensity, saturation, scratches, cracks, and for searching the database for records corresponding to the selected at least one chip parameter.

A further embodiment of the present invention provides a method for assessing the quality of gene expression data comprising the steps of: assessing the number of probe pairs having a mismatch value and a perfect match value, for which the mismatch value is greater than the perfect match value; and assessing a ratio of the natural log of a mean intensity of non-control oligonucleotides to the natural log of an image fifth percentile.

Another embodiment of the present invention provides an automated method for masking a defective area on a chip, comprising the steps of: receiving an input from a user to launch a masking application where the defective area is less than five percent of an image of the chip; providing a selection for a mask shape, wherein the mask shape is chosen from the group consisting of an ellipse and rectangle; receiving an input from the user to enclose the defective area with the selected mask shape; displaying a query requesting a description of the defective area; receiving an input from the user providing the description; and load information regarding the defective area into a database.

BRIEF DESCRIPTION OF THE DRAWINGS

Understanding of the present invention will be facilitated by consideration of the following detailed description of preferred embodiments of the present invention taken in conjunction with the accompanying drawings, in which like numerals refer to like parts and in which:

FIG. 3 is an exemplary screen shot of a main screen of an embodiment of the present invention;

FIGS. 4A-F are sections of a spreadsheet illustrative of an embodiment of the present invention;

FIG. 5 shows a Chip Process table layout of an embodiment of the present invention;

FIG. 6 shows a controlled vocabulary table for processes of an embodiment of the present invention;

FIG. 7 shows an exemplary controlled vocabulary table for problems of an embodiment of the present invention;

FIG. 8 shows an exemplary Chip table layout of an embodiment of the present invention;

FIG. 9 shows an exemplary Defect table layout of an embodiment of the present invention;

FIG. 10 shows an exemplary Defect ROI table layout of an embodiment of the present invention;

FIG. 11 shows an exemplary table of reasons for failing a chip or masking a region of an embodiment of the present invention;

FIG. 12 shows an exemplary table of fields used by an embodiment of the present invention;

DETAILED DESCRIPTION OF THE PREFERRED EMBODIMENTS

The present invention relates to evaluation and manipulation of gene expression data obtained from scanning of intensities of patterned microarrays of hybridized oligonucleotide probes. The terms "microarray", "array" and "chip" are used interchangeably throughout the description to refer to such microarrays, an example of which is the GeneChip® microarray that is commercially available from Affymetrix, Inc., Santa Clara, Calif., USA.

In a preferred embodiment, the present invention may be used in conjunction with a system and method for analysis of gene expression data. One example of such a system and method is the Gene Express® Software System and the Genesis™ Enterprise System, which are commercially available from Gene Logic Inc, Gaithersburg, Md. Such systems and methods are the subject of pending patent applications including U.S. application Ser. No. 09/862,424, filed May 23, 2001, Ser. No. 10/090,144, filed Mar. 5, 2002, and Ser. No. 10/096,645, filed Mar. 14, 2002, and PCT application Serial No. US02/19877, filed Jun. 24, 2002. The disclosures of each of the foregoing applications are incorporated herein by reference in their entireties. The cited examples are not intended to be limiting and other similar systems and methods which would benefit from the improvements provided by the present invention are commercially-available or have been described in the literature.

Figure 1:
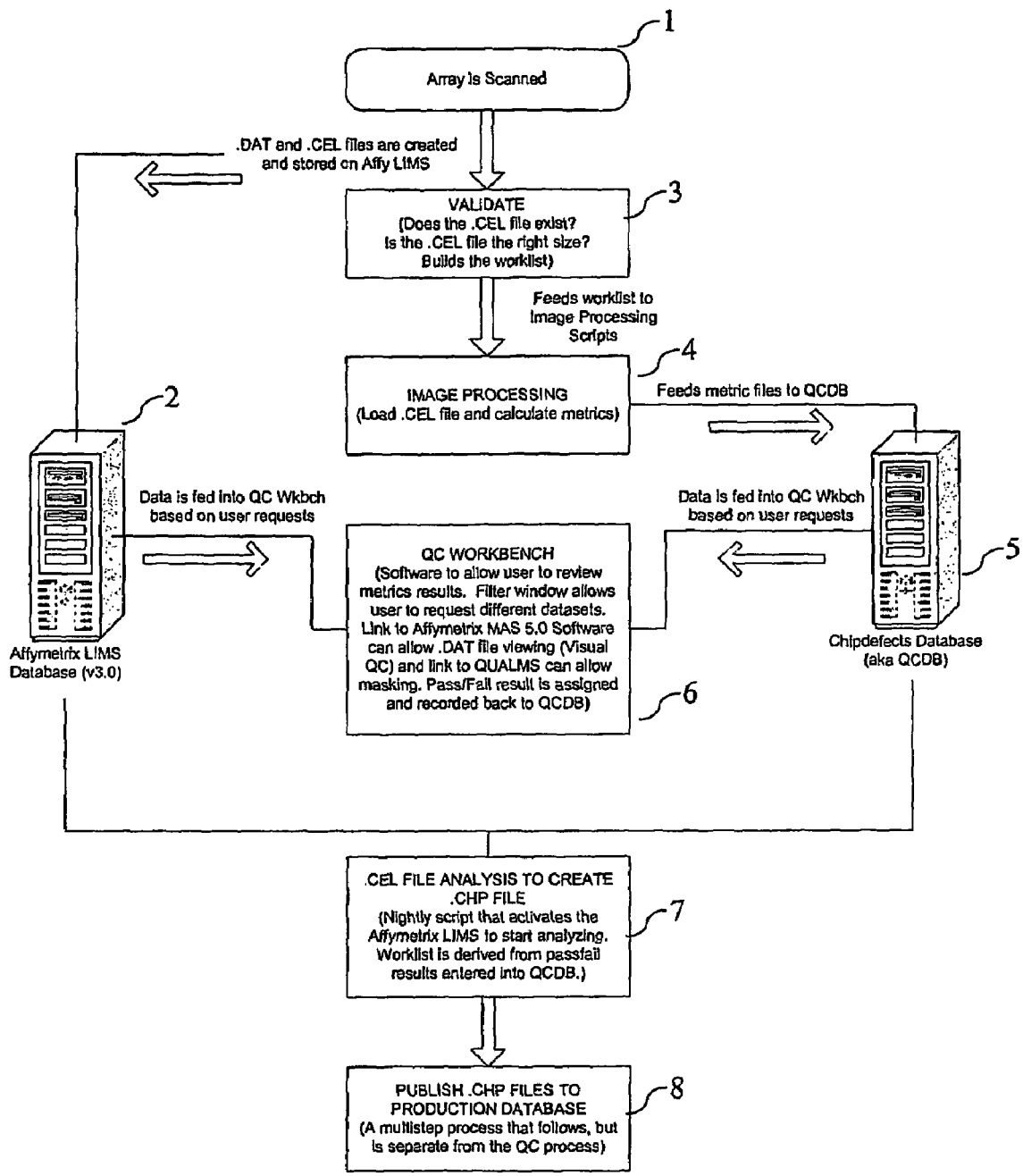
FIG. 1 is a process flow diagram of an embodiment of the present invention.

FIG. 1 illustrates a flow process for an embodiment of the present invention. Referring to FIG. 1, the array is scanned 1, thereby creating files, for example, a DAT image file and an associated CEL (cell intensity) file containing probe intensity data and stored on, for example, Affymetrix® Laboratory Information Management System ("LIMS") Database (v3.0) 2. Pre-Visual QC validation 3 is performed during which the CEL file is checked for basic integrity, for example, whether the CEL file exists and whether the CEL file is the right size. A worklist listing the CEL files for which QC evaluation is desired is assembled and input into Image Processing (IP) 4. In IP 4, the CEL file is loaded and the metrics, e.g., intensity, are calculated. The metrics are then input to a QC database, QCDB 5, for example, a Chipdefects Database. Based on user requests, data from both the QCDB 5 and the Affymetrix® LIMS Database 2 are input to software application 6. Software application 6 allows users to review metrics results, and provides, for example, a filter window to enable the user to request different datasets. In one embodiment, the Affymetrix® Microarray Suite Version 5.0 ("MAS 5.0") software (Affymetrix, Inc., Santa Clara, Calif.) may be used for viewing. This link provides means for DAT file viewing for visual QC. A link to software is also provided for executing a masking routine program, outputting a modified CEL file with masked probe data to exclude the flagged defective probes/regions. Pass/Fail results are assigned and recorded back to the QCDB 5 and the CEL file is regenerated if missing. Next, the CEL file analysis 7 generates, for example, CHP (analysis output) files. In one embodiment, the Affymetrix® LIMS (v)3.0) is part of a regularly scheduled scripting process using the Affymetrix® LIMS 3 API (application programming interface). In other embodiments, a similar function may be performed manually using Affymetrix's "Analysis" web interface. In the next step, the CHP files are published to a production database 8. Other post-publication processes can include Consistency Check, CopyOut, Staging, and DataWarehouse, which is part of the Gene Express® Software System.

Figure 2:
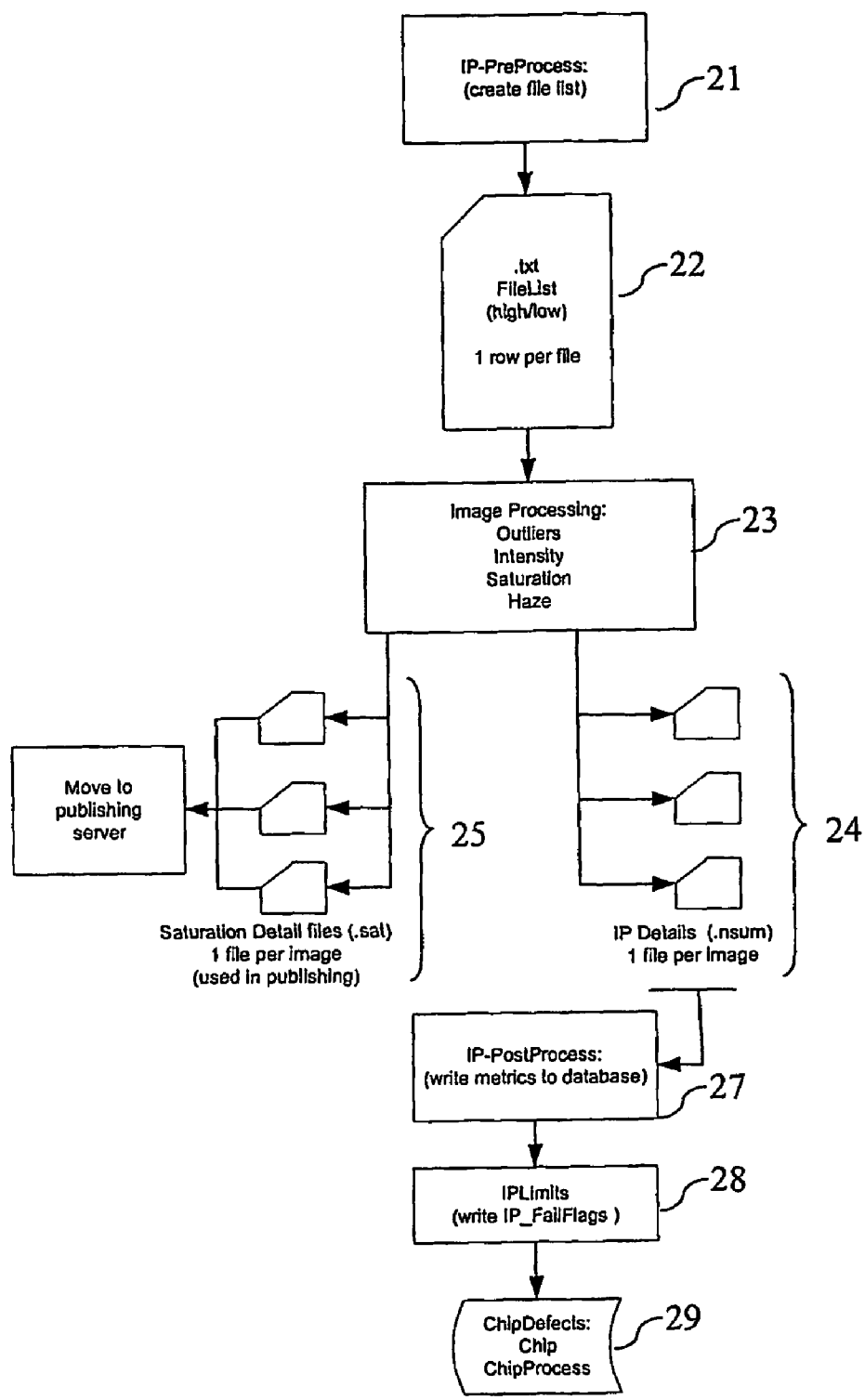
FIG. 2 is an image processing workflow diagram of an embodiment of the present invention.

FIG. 2 illustrates an image processing workflow of an embodiment of the present invention. Image processing metrics are used for detecting overall chip quality as well as identifying specific defect areas on a chip. In addition, saturation calculations are calculated during this process as well. In one embodiment, the image processing runs as a scheduled batch process on an input queue of files. The input is a list 21 of experiments generated by the validation batch process shown as step 3 in FIG. 1. For each experiment, the CEL file name is passed to an automated quality control (autoqc.exe) routine, which generates a text file (.nsum) 22 containing the metrics. A script then reads the .nsum file and saves the metrics in the Chip table of the ChipDefects database. The entire process is shown in FIG. 2 (21-29). In the present embodiment, one metric, "Spike-in $R^2$, is calculated differently depending on whether high or low scanner settings were used. Both values are calculated; however, only the scanner setting that was actually use is stored in the database.

The most commonly encountered defects in microarray measurements are:
1) high mismatch intensity ("HMI")—the count of the number of probe pairs in which the Mismatch probe intensity is greater than the Perfect Match probe intensity;
2) snow—a collection of bright focused (usually 2-4 pixels in size, less than the size of a probe cell) pixels either concentrated in an area or distributed across the chip image;
3) low signal-to-noise ratio (SNR)—the ratio of the log of the average probe cell intensity to the log of the 5th percentile probe cell intensity. Assesses how bright the chip is in comparison to the background level;
4) non-linearity—a distortion in the .DAT image that adversely affects the software's ability to place a uniform grid over the image. Detected by assessing the distribution of outliers on an array;
5) bright locally—a region of high intensity that obscures the true signal of the probes in that area;
6) crop circle—a specific type of dim local defect. A round (or sometimes pseudo-rectangular) region of darkness in the center of the array that typically spans ⅓ to ½ of the .DAT image;
7) haze—a form of bright local defect in which the brightness is less severe. The brightness may appear to be a region of higher background intensity, but not so intense that probe cells of average intensity cannot be distinguished.
8) dim locally—A region of low intensity that obscures the true signal of the probes in that area.
9) processing degradation—May be due to compromised sample quality (indicated by 5'/3' ratios) or poor equipment performance (scanner linearity, fluidics staining). Several metrics can contribute to these kinds of defects.

A number of different metrics that can be used for flagging such common defects are listed in Table A below along with the defect(s) that can be detected using that given metric. The order in which the metrics are listed in the table or the following description is not intended to suggest or imply a level of importance or preference. The term "Spike-In" referenced in several of the metrics refers to certain polynucleotides that are used in normalizing the hybridization reactions that generate the DAT image files. Such polynucleotides and methods for making and using them, as well as the eleven preferred spike-ins, are disclosed in PCT application PCT/US02/17813, filed on Jun. 6, 2002, and published as WO 02/099071 A2 on Dec. 12, 2002, the disclosure of which is incorporated herein by reference in its entirety.

TABLE A

| METRIC | TARGET DEFECT(S) |
| --- | --- |
| 1 Oligo B2 Mean Intensity | Bright artifacts |
| 2 Spike-In Offset | Dim chips, some bright artifacts. |
| 3 Spike-In Slope | Dim chips, crop circles. |
| 4 Spike-In Coeff. of Determination ($R^2$) | Crop circles, bright & dim artifacts, grid misalignment. |
| 5 Spike-In Coeff. of Determination ($R^2$) - 9 Spike-ins | Crop circles, bright & dim artifacts, grid alignment. |
| 6 Spike-In Mean | Dim chips. |
| 7 Mean Intensity of Non-control Oligos | Dim chips. |
| 8 Probe Pair Diff. Outlier Count | Crop circles, grid misalignment, dim artifacts. |
| 9 Negative Probe Pair Count | Dim chips, expression data quality |
| 10 Vert. P10 Peak to Median Ratio ("Haze Band Metric") | Haze bands, some grid misalignment. |
| 11 Max/Min Ratio for Horiz. P25 Profile | Crop circles, scanner failure, haze. |
| 12 Max/Min Ratio for Vert. P25 Profile | Dim chips, some misaligned chips. |
| 13 2 Edge Ratios for Horiz. P25 Profile | Scanner failure, haze, bright; dim artifacts, crop circles. |
| 14 2 Edge Ratios for Vert. P25 Profile | Haze, bright & dim artifacts, crop circles |
| 15 Max/Min Ratio for Horiz. P75 Profile | Dim artifacts, crop circles, some haze. |
| 16 Max/Min Ratio for Vert. P75 Profile | Misalignment (possibly). |
| 17 2 Edge Ratios for Horiz. P75 Profile | Scanner failure, haze, bright artifacts |
| 18 2 Edge Ratios for Vert. P75 Profile | Crop circles, some artifacts. |
| 19 Probe Pair Diff. Outlier Vert. Variance | Dim artifacts |
| 20 Probe Pair Diff. Outlier Horiz. Variance. | Misalignment, dim & bright artifacts, scanner failure, crop circles |
| 21 Vert. Probe Pair Diff. Outlier Edge Ratios | Some bright artifacts |
| 22 Horiz. Probe Pair Diff. Outlier Edge Ratios | Dim artifacts, misalignment, scanner failure. |
| 23 Image P5 | High background |
| 24 No. of Saturated Probes | Chips too bright for linear response |
| 25 5'3' Ratio for GAPDH | General sample problem, no specific defect. |
| 26 5'3' Ratio for Beta Actin | General sample problem, no specific defect. |
| 27 Mean Av. Diff. | Dim chips. |
| 28 SNR (Signal to Noise Ratio) | Dim chips. |
| 29 Ln(Brightness)/ln(P5) | Dim chips. |
| 30 Neg. Probe Pair Horiz. & Vert. Variance | Dim artifacts, some bright artifacts. |
| 31 Neg. Probe Pair Horiz. & Vert. Max./Median Ratio | Bright and dim artifacts. |
| 32 Affymetrix Outlier Count | Grid misalignment, scanner failure. |
| 33 Affymetrix Outlier Horiz. & Vert. Variance. | Grid misalignment |
| 34 Affymetrix Outlier Horiz. & Vert. Max. | Crop circles, grid misalignment |
| 35 Probe Pair Diff. Profile Product Max. | Bright artifacts |
| 36 Affymetrix Outlier Profile Product Max. | Snow |
| 37 P25/P50/P75 Profile Product Max. | Haze, local darkness |
| 38 Median of Mean/SD for PM & MM Cells | Low SNR |
| 39 Product Maxima for Li-Wong Outliers, Cell File Outliers, P50 & P75 | Snow, local defects. |
| 40 Horiz. Variance of LWPM Outliers | Scratches, cracks. |
| 41 Local Background Normalized Variance: | Bright artifacts |
| 42 Est. Background Exterior to Interior Ratio | Crop circles. |

The algorithm for determining each of the metrics listed in Table A is described below:

1. Oligonucleotide B2 Mean Intensity: The mean intensity of type 15 oligonucleotide B2 cells around the perimeter of the cell region can be used to flag some bright artifacts.

2. Spike-In Offset: The value of α for which the log of the spike-in average difference, excluding oligonucleotide B2 cells, is given by α+β.ln(spike-in concentration) where β is the spike-in slope, can be used to flag some dim chips and some bright artifacts. Currently, there are 11 preferred spike-ins. See PCT application number WO 02/099071 A2 as referenced above.

3. Spike-In Slope: The value of β as given above in #2 can be used to flag dim chips and crop circle chips.

4. Spike-In Coefficient of Determination ($R^2$): For flagging crop circles, bright and dim artifacts and grid misalignment, the value of $R^2$ determined as follows can be used:

$$R^2 = \frac{\sum_i (\log(Av.Diff.(i)) - \alpha' - \beta' \cdot \ln(Conc.(i)))^2}{\sum_i (\log(Av.Diff.(i)) - \log(Av.Diff.(\text{Mean})))^2} \quad (3)$$

where α' and β' are the estimated values of α and β respectively, and i is the spike-in index.

5. Spike-In Coefficient of Determination ($R^2$) with 9 Spike-ins: The value of $R^2$ calculated as above but using spike-ins that were spiked at the 9 lowest concentrations.

6. Spike-In Mean: Mean value over the spike-ins of the (spike-in average difference divided by the spike-in concentration) can be used to flag some dim chips.

7. Mean Intensity of Non-control Oligonucleotides: The mean value of the combined PM and MM cells for all non-control oligonucleotides can be used to flag dim chips.

8. Probe Pair Difference Outlier Count: The count of the Probe Pair Difference chip outliers using a method derived from Li & Wong as previously described (for the non-MM model) can be used to flag crop circles, grid misalignment and dim artifacts. When determining this count, Probe Pair Difference model outliers and negative probe pairs, which are probe pairs having a mismatch mean greater than that of the corresponding perfect match probe, are never considered.

9. Negative Probe Pair Count: The number of probe pairs for which the MM value is greater than the PM value can be used to flag dim chips and provides a measure of expression data quality.

10. Vertical $10^{th}$ Percentile Peak to Median Ratio ("Haze Band Metric"): The ratio of the maximum to median value along the 1D vertical $10^{th}$ percentile profile can be used to flag haze bands and some grid misalignment. The vertical $n^{th}$ percentile profile is made by taking the $n^{th}$ percentile cell values, including both PM and MM, for pairs of rows and assigning the result to an incrementing Y coordinate of a 1D vertical profile. The first 20 rows are omitted to avoid control oligos.

11. Max/Min Ratio for Horizontal $25^{th}$ Percentile Profile: The ratio of the maximum to minimum value along the 1D horizontal $25^{th}$ percentile profile can be used to flag crop circles, scanner failure and haze. The horizontal $n^{th}$ percentile profile is made by taking the $n^{th}$ percentile cell values, including both PM and MM, for pairs of columns and assigning the result to an incrementing X coordinate of a 1D horizontal profile.

12. Max/Min Ratio for Vertical $25^{th}$ Percentile Profile: The ratio of the maximum to minimum value along the 1D vertical $25^{th}$ percentile profile can be used to flag dim chips and some misaligned chips.

13. Two Edge Ratios for Horizontal $25^{th}$ Percentile Profile: The ratio of the mean of the first and last 5% of the horizontal $25^{th}$ percentile profile to the overall mean of the profile can be used to flag scanner failure, haze, bright and dim artifacts and crop circles.

14. Two Edge Ratios for Vertical $25^{th}$ Percentile Profile: The ratio of the mean of the first and last 5% of the vertical $25^{th}$ percentile profile to the overall mean of the profile can be used to flag haze, bright and dim artifacts and crop circles.

15. Max/Min Ratio for Horizontal $75^{th}$ Percentile Profile: The ratio of the maximum to minimum value along the 1D horizontal $75^{th}$ percentile profile can be used to flags dim artifacts, crop circles and some haze.

16. Max/Min Ratio for Vertical $75^{th}$ Percentile Profile: The ratio of the maximum to minimum value along the 1D vertical $75^{th}$ percentile profile can possibly be used to flag misalignment.

17. Two Edge Ratios for Horizontal $75^{th}$ Percentile Profile: The ratio of the mean of the first and last 5% of the horizontal $75^{th}$ percentile profile to the overall mean of the profile can be used to flag scanner failure, haze, and bright artifacts.

18. Two Edge Ratios for Vertical $75^{th}$ Percentile Profile: The ratio of the mean of the first and last 5% of the vertical $75^{th}$ percentile profile to the overall mean of the profile can be used to flag crop circles and some artifacts.

19. Probe Pair Difference Outlier Vertical Variance: The variance value $\sigma^2$ given by the following formula can be used to flag dim artifacts:

$$\frac{\left(\sum_i (y_i - \mu_y)^2\right)}{(N-1)}, \qquad (4)$$

where $y_i$ is the $i^{th}$ bin of the vertical Probe Pair Difference outlier distribution histogram, N is the number of histogram bins and $\mu_y$ is the mean count for the histogram bins. The vertical outlier distribution histogram is formed by dividing the array into a selected number (default=100) of horizontal regions (or "bins") and counting the number of outliers in each bin. (The bins correspond to the histogram bins.)

20. Probe Pair Difference Outlier Horizontal Variance: The variance value $\sigma^2$ given by the following formula can be used to flag misalignment, dim and bright artifacts, scanner failure and crop circles:

$$\frac{\left(\sum_i (x_i - \mu_x)^2\right)}{(N-1)}, \qquad (5)$$

where $x_i$ is the $i^{th}$ bin of the horizontal Probe Pair Difference outlier distribution histogram, N is the number of histogram bins and $\mu_x$ is the mean count for the histogram bins. The horizontal outlier distribution histogram is formed by dividing the array into a certain number (default=100) of vertical regions (or "bins") and counting the number of outliers in each bin. (The bins correspond to the histogram bins.)

21. Vertical Probe Pair Difference Outlier Edge Ratios: The ratio of the mean of the first and last 5% of the vertical Probe Pair Difference outlier distribution histogram to the overall mean of the histogram can be used to flag some bright artifacts.

22. Horizontal Probe Pair Difference Outlier Edge Ratios: The ratio of the mean of the first and last 5% of the vertical Probe Pair Difference outlier distribution histogram to the overall mean of the histogram can be used to flag dim artifacts, misalignment and scanner failure.

23. Image $5^{th}$ Percentile: The $5^{th}$ percentile value of the intensity over all non-control PM and MM cells of the image can be used to flag high background.

24. Number of Saturated Probes: The number of PM and MM probes with intensity greater than 46,000 can be used to flag chips that are too bright to provide a linear response.

25. 5'3' Ratio for GapDH: In laboratory processing, RNAses will degrade the RNA starting at the 5' end progressing toward the 3' end. When samples are optimally processed, there should be equal representation of both 5' and 3' ends, such that the ratio should be approximately 1. When samples are processed poorly, degradation occurs and there is less representation of the 5' end relative to the 3' end, so that the ratio is less than 1. The ratio of average difference of 5' fragment to that of 3' fragment for the housekeeping gene GapDH can be used to flag grid misalignment and crop circles.

26. 5'3' Ratio for Beta Actin: The ratio of average difference of 5' fragment to that of 3' fragment for another housekeeping gene, Beta Actin, does not flag a specific defect, but can indicate a general problem with sample processing for the reasons described above.

27. Mean Av. Diff.: Arithmetic mean, between the $2^{nd}$ and $98^{th}$ percentiles, of the average difference of all fragments on the chip can be used to flag dim chips.

28. SNR (Signal to Noise Ratio): The ratio of the mean intensity of non-control oligonucleotides to the image $5^{th}$ percentile can be used to flag dim chips.

29. Ln(Brightness)/ln(P5): The ratio of the natural log of the mean intensity of non-control oligonucleotides to the natural log of the image $5^{th}$ percentile, i.e., the log-based SNR, can be used to flag dim chips. The overall brightness of the chip reflects both the signal due to specific hybridization (SH) and the background due to non-specific hybridization (NH). Since SH lights up the target cells in a continuum of different ways, depending on the quantity of target gene fragment present, the overall brightness of the non-control oligonucleotides on the chip can be taken as a metric for signal strength. It has been observed that brightness and background tend to have more of a log-normal distribution than a normal distribution and that the ratio of log-transformed values are more normal than is the ratio of the linear values. Therefore, the signal values are log transformed before taking the ratio.

30. Negative Probe Pair Horizontal and Vertical Variance: These variance values are calculated as above for the corresponding variances for Probe Pair Difference outliers, however, negative probe pairs are used instead of Probe Pair Difference outliers. The variance values can be used to flag dim artifacts and some bright artifacts.

31. Negative Probe Pair Horizontal and Vertical Maximum/Median Ratio: The ratio of the maximum value to that of the median value of the horizontal or vertical negative probe pair distribution histogram can be used to flag bright and dim artifacts. The negative probe pair distribution histograms are made in the same way as the outlier distribution histograms except that the negative probe pairs are used instead of outliers.

32. Affymetrix Outlier Count: The number of outliers listed in the Affymetrix cell file (also called CEL file) can be used to flag misalignment and scanner failure.

33. Affymetrix Outlier Horizontal and Vertical Variance: These variance values are determined in a similar manner as are the corresponding variances for Probe Pair Difference outliers, but using Affymetrix cell file outliers instead of Probe Pair Difference outliers. Grid misalignment has a strong tendency to form a vertical band slightly displaced from the left edge of the array. This results in a vertical band of outliers. Therefore, the presence of grid misalignment raises the horizontal variance of the cell file outliers across the array, providing flags for grid misalignment.

34. Affymetrix Outlier Horizontal and Vertical Maximum: The maximum values of the horizontal or vertical Affymetrix outlier distribution histogram can be used to flag crop circles and grid misalignment.

35. Probe Pair Difference Profile Product Maximum: The maximum of a matrix formed by vector multiplication of the vertical and horizontal Probe Pair Difference outlier distribution profiles can be used to flag localized defects such as bright artifacts.

36. Affymetrix Outlier Profile Product Maximum: The maximum of a matrix formed by vector multiplication of the vertical and horizontal Affymetrix cell file outlier distribution profiles can be used to flag snow. While snow cannot usually be seen in cell file images, it tends to generate cell file outliers by producing very high $75^{th}$ percentiles within affected cells, i.e., the cell file outliers are concentrated where the snow is worst. The part of the array affected by snow will be reflected in the peak value in both horizontal and vertical profile of the outlier distribution. The product maximum is given by $P_{max} = \max(H_x H_y, \forall x,y)$, where $H_x$ is the value of the horizontal profile corresponding to the x-coordinate x and $H_y$ is the value of the vertical profile corresponding to the y-coordinate y. A high value for $P_{max}$ indicates snow.

37. P25/P50/P75 Profile Product Maximum: The maximum of a matrix formed by vector multiplication of the vertical and horizontal $25^{th}$ percentile/$50^{th}$ percentile/$75^{th}$ percentile profiles can be used to flag a number of defects. The horizontal $25^{th}$ percentile profile tends to reflect horizontal variation of the darker cells horizontally across the image. Haze tends to increase the overall brightness of the image along the edges, particularly the vertical edges. This has more impact on the darker cells since the brighter cells are more likely to become saturated. While haze very rarely impacts the entire image, it tends to impact the left, and sometimes the right, edge of the image more than the rest of the image.

The horizontal $75^{th}$ percentile profile reflects the horizontal variation of the brighter cells horizontally across the image. Artifacts that produce locally dark regions have more impact upon these cells since dark cells are closer to zero intensity and cannot become much darker. Hence, variation in the horizontal $75^{th}$ percentile profile is a sensitive metric for local darkness.

38. Median of Mean/SD for PM and MM Cells: For each PM (or MM) cell, the intra-cell mean is divided by the intra-cell standard deviation. The median of the results is determined first over all the PM cells, then over all the MM cells. These values can be used to flag low signal to noise ratio.

39. Product Maxima for Li-Wong Outliers, Cell File Outliers, $50^{th}$ Percentile and $75^{th}$ Percentile: For every xy coordinate on the cell file plane, the value of the x-coordinate of the horizontal profile is multiplied by the y-coordinate of the vertical profile. The measurement is the maximum over all the xy coordinates which can be used to flag snow and local defects.

40. Horizontal Variance of LWPM Outliers: The LWPM (Li-Wong PM) outliers are determined in the same manner as Li-Wong outliers, however only PM probes are considered rather than probe pairs such that the PM value is used instead of the probe pair difference. The variance value can be used to flag scratches and cracks.

41. Local Background Normalized Variance: This metric is based on a model which estimates the local background B and its spatial variation. The procedure for local background estimation is described in detail below. The normalized variance, $\sigma^2$, is given by $$\sigma^2 = \frac{\sum_{xy}(B_{xy} - \mu_B)^2}{\mu_B}, \qquad (6)$$

where $B_{xy}$ is the estimated background intensity at coordinates xy and $\mu_B = (\Sigma_{xy}(B_{xy}))/N$, where N is the total number of pixels in the background image. The background variance is normalized with respect to the mean background intensity in order to decouple background variance from high background intensity, which can be used to flag bright artifacts.

42. Estimated Background Exterior to Interior Ratio: The ratio of the mean intensity of the outer third of the estimated background image to that of the inner third can be used to flag crop circles.

Estimated Background B

The basis of the estimated background technique is that the intensity of each PM probe may be given by the following equation:

$$P_{ijk} = (\theta_i \phi_j)_k + B + v_{jk} \tag{7}$$

where $P_{ijk}$ is the brightness (intensity) of the PM probe, $\theta_{ik}$ is the model-based expression index (MBEI) of fragment k in array i and $\phi_{jk}$, the probe sensitivity index (PSI) of probe j of fragment f is the derivative of the response of the $j^{th}$ probe for fragment k with respect to the MBEI. (The symbolism used here roughly follows the Li-Wong convention except that $\phi_{jk}$ denotes the PSI of PM probe j of fragment k.) B is the local background intensity and $v_{jk}$ is the estimate of the baseline response of PM probe j of fragment k.

B and v are given, respectively, by:

$$B = \begin{cases} \text{Model1} & B_{i(xy)fk} \\ \text{Model2} & 0 \\ \text{Model3} & B_i \\ \text{Model4} & B_{ijk} \\ \text{Model5} & B_{ijk} \end{cases} \tag{8}$$

$$v = \begin{cases} \text{Model1} & 0 \\ \text{Model2} & 0 \\ \text{Model3} & 0 \\ \text{Model4} & 0 \\ \text{Model5} & v_{jk} \end{cases} \tag{9}$$

where $B_{i(xy)_{jk}}$ is the estimated background at cell coordinates (xy) on array i, $B_i$ is the first percentile of all non-control probes in array i and $B_{ijk}$ is the estimated background at probe j of fragment k on array i. For QC implementation, Model4 is used.

The inverse solution for equation (7) is only well posed if some constraint is placed upon the $\phi_{jk}$ values. In the exemplary embodiment, the constraint used is the same as that used by Li and Wong, which is:

$$\sum_{j=1}^{J} \phi_j^2 = J, \forall k, \tag{10}$$

where J is the number of PM probes for fragment k. To obtain initial estimates for $\phi_{jk}$, $\forall j,k$, first determine the sensitivity ratio $s_{jk}$ of each probe relative to the first probe of the corresponding fragment.

$$s_{jk} = \frac{\phi_{jk}}{\phi_{1k}} \approx \frac{\sum_{i=1}^{I} \frac{P(xy)_{ijk}}{P(xy)_{i1k}}}{I}. \tag{11}$$

Combining equations (10) and (11) yields:

$$\phi_1 = \sqrt{\frac{J}{\sum_{j=1}^{J} s_j^2}}. \tag{12}$$

Initial estimates of $\phi_j$, j>1 can be found using equation (11). Estimates of $\theta_{ik}$, $\forall i,k$ can be found using $$\begin{bmatrix} \theta_{1k} \\ \theta_{2k} \\ \vdots \\ \theta_{Ik} \end{bmatrix} = \begin{bmatrix} \Phi_1 \\ \Phi_2 \\ \vdots \\ \Phi_I \end{bmatrix}^{-1} \begin{bmatrix} \Psi_1 \\ \Psi_2 \\ \vdots \\ \Psi_I \end{bmatrix}, \tag{13}$$

where $\Phi_i$ is a J×I matrix for which column i is given by:

$$\begin{bmatrix} \phi_{1k} \\ \phi_{2k} \\ \vdots \\ \phi_{Jk} \end{bmatrix} \tag{14}$$

and the other columns are all zeros. $\Psi_i$ is given by:

$$\begin{bmatrix} \psi_{i1k} \\ \psi_{i2k} \\ \vdots \\ \psi_{ijk} \end{bmatrix}, \text{ where } \psi_{ijk} = \begin{cases} P_{ijk} - B & \text{if } P_{ijk} > B \\ 0 & \text{otherwise.} \end{cases} \tag{15}$$

For Model4 and Model5, the following background estimate may be used as a starting point:

$$B_{i(xy)_{jk}} = \frac{2H_x V_y}{H_x + V_y}, \tag{16}$$

where $H_x$ is the $x^{th}$ element of the horizontal profile, $V_y$ is the $y^{th}$ element of the vertical profile, and $(xy)_{jk}$ are the spatial coordinates of the $j^{th}$ PM probe of the $k^{th}$ fragment. For Model4, $v_{jk}=0$, $\forall j,k$. For Model5, $v_{jk}$, $\forall j,k$ is estimated using $$v_{jk} = I^{-1} \sum_{i=1}^{I} (P_{ijk} - \theta_{ik}\phi_{jk} - B_{ijk}). \tag{17}$$

If equation (17) $v_{jk}<0$, $v_{jk}$ is set to zero and the following procedure is iterated until some predefined criterion, such as the total number of iterations, e.g., 10 to 20 or fewer, or when the rate of change falls below a certain value, is met. Estimate $\phi_{jk}$, $\forall j,k$ using $$\phi_{jk} = I^{-1} \sum_{i=1}^{I} \frac{(P-B)_{ijk} - v_{jk}}{\theta_{ik}}. \tag{18}$$

To maintain stability, this refinement is only performed if $\theta_{ik}$ is above a certain threshold. According to the preferred embodiment, a reasonable threshold is 1.0.

Next, estimate the background $B_{ijk}$, $\forall i,j,k$ using $$B_{ijk}=P_{ijk}-\theta_{ik}\phi_{jk}-\nu_{jk}. \quad (19)$$

If equation (19) returns a negative background value, the previous background value is retained. The array image is then spatially filtered using a median filter. $\theta_{ik}$, $\forall i,k$ is estimated using $$\begin{bmatrix} \theta_{1k} \\ \theta_{2k} \\ \vdots \\ \theta_{lk} \end{bmatrix} = \begin{bmatrix} \Phi_1 \\ \Phi_2 \\ \vdots \\ \Phi_I \end{bmatrix}^{-1} \begin{bmatrix} Y_1 \\ Y_2 \\ \vdots \\ Y_I \end{bmatrix}, \quad (20)$$

where $\Phi_n$ is the same as for equation (13) and $Y_n$ is given by $$\begin{bmatrix} \upsilon_{n1k} \\ \upsilon_{n2k} \\ \vdots \\ \upsilon_{nJk} \end{bmatrix} \text{ where } \upsilon_{ijk} = P_{ijk} - \nu_{jk} - B_{ijk}. \quad (21)$$

Some criterion is necessary to stop the iterations. The sum of the local background changes tends to fall rapidly with the first few iterations, then levels off due to inevitable changes arising from median filtering. In the exemplary embodiment, the iterations are stopped when the sum of these changes falls below a certain value as the cube of the number of arrays.

Due to the large amount of available data, it is not practical to process all of the arrays in groups. Further, some arrays are so defective that they may compromise an accurate determination of the parameters for the group. To address these issues, a model can be constructed for each type of chip using high quality chips from a wide range of tissues. This model can then be used to process subsequent arrays. The model contains the $\phi$ values and, where appropriate, the $\nu$ values for each chip type. For an individual array, the $\phi$ (and $\nu$) values are read from the model and held constant. The other variables are refined as described above for each of the models with I=1.

Robust Multi-array Averaging (RMA) can be used to provide additional metrics that can be incorporated in a QC evaluation. RMA uses a set of arrays, e.g., all available samples (if less than 40) or 40 randomly selected samples for each transcript, tissue, and chip type, and obtains a log scale measure of expression using the PM probe pairs in each array. (See, e.g., frizzary, et al., "Exploration, Normalization, and Summaries of High Density Oligonucleotide Array Probe Level Data," *Biostatistics,* 4:249-264 (2003), and frizzary, et al., "Summaries of Affymetrix GeneChip® Probe Level Data," *Nucleic Acids Research,* 31:e15 (2003), both of which are incorporated herein by reference in their entirety.) We have modified RMA by using a training set of cell files for each array and tissue type to construct a model that is applied to PM probe values. This modified RMA analysis involves the following steps:

Step 1: A set of arrays are background-corrected according to the following equation:

$$P_0 = \hat{P} + \frac{\frac{\sigma_B}{\sqrt{2\pi}}\left(e^{-0.5\left(\frac{\hat{P}}{\sigma_B}\right)}\right)}{PNorm\left(\frac{\hat{P}}{\sigma_B}\right)}, \quad (22)$$

where $P_0$ is the background-corrected value of a PM probe and PNorm(x) is the pnorm value (see *Applied Statistics Algorithms* (1985) P. Griffiths and I. D. Hill, eds.) of a given floating point value, x, and $$\hat{P}=P_i-(\mu_B+\alpha_B\sigma_B^2), \quad (23)$$

where $P_i$ is the initial value of the PM probe and $\mu_B$ is the left-hand mode (the distribution that is left of the main mode) of all the input PM values. $\sigma_B$ is the standard deviation of the input PM values to the left of $\mu_B$. $\alpha_B$ is the reciprocal of the expressor mean, which is the mode of the distribution obtained by subtracting $\mu_B$ from every element of the distribution to the right of $\mu_B$.

Step 2: The background-corrected arrays are normalized using quantile normalization. The normalization vector, for each chip and sample type, is made as follows: (1) for each of the cell files that is used for the training set (to build the model), make a vector consisting of the (mean) values of all the PM cells; (2) order each vector in ascending order; (3) the normalization vector has the length of each of these vectors and consists of the median value of the corresponding element of each sample vector; and (4) the normalization vector is stored in a file and used to normalize all cell files, of that chip and sample type, that are processed. (Also, see, Bolstad, "Probe Level Quantile Normalization of High Density Oligonucleotide Probe Data", (2001), www.stat.berkeley.edu/~bolstad/stuff/qnorm.pdf, which is incorporated herein by reference in its entirety.)

Step 3: The resulting arrays are $\log_2$ (log-base 2) transformed.

Step 4: For each gene fragment (probe set), a sub-matrix is formed with a row for each PM probe in the probe set and a column for each array in the array set.

Step 5: Using the sub-matrix as input, median polish is used to estimate the model parameters for the probe set. Median polish is a robust procedure that uses medians rather than means for summaries, making the summaries resistant to outliers. (See Holder, et al., "Statistical analysis of high density oligonucleotide arrays: a SAFER approach", *Proc. ASA Annual Meeting,* Atlanta, Ga. (2001), which is incorporated herein by reference.)

The model parameters derived from median polish for each probe set are:

Probe effects (alpha values) from the fitted row probes.
The scale derived from the residuals matrix.
Median weight factor, which is obtained as follows:
  Divide the absolute values of the median polish residuals matrix by the scale factor.
  Obtain the weight matrix by applying the Huber Psi model to the result. (See, e.g., P. J. Huber (1981) *Robust Statistics.* Wiley, incorporated herein by reference.)
  Take the square root of the reciprocal of the sum of each column across the rows of the weight matrix.
  Take the median value of the results.

Step 6: Once the model is fitted, each array to be analyzed is background corrected, normalized and log transformed as for each array of the model set. The model is applied to an input sample as follows: (1) form a vector (sample vector)

from all the PM values (means) for the input cell file; (2) order the vector in ascending order but note which PM cell each vector element relates to and (3) replace each PM cell value with the value, in the normalization vector, with the same index as that PM cell's entry in the ordered sample vector.

Step 7: A vector is formed for the PM probe values of each gene fragment.

Step 8: A residual vector is formed by subtracting from each element of the fragment vector the value predicted by the model. (This removes the probe effect.)

Step 9: Subtract the median of the residual vector from each element of the vector. This removes the chip effect by centering the residuals, if any remain. (This cannot be done across chips.)

Step 10: Obtain absolute values of vector elements.

Step 11: Divide results by the model scale value.

Step 12: Apply the Huber Psi model to obtain a weights vector.

The elements of the weights vector range in value from 0 to 1 and represent the quality of the associated PM probe. Good probes also tend to have a high residual. Weight factor for each transcript appears to be a better QC metric for probes and is determined by:

$$\overline{w} = \frac{1}{\sqrt{\sum_{j=1}^{J} w_j}}, \quad (24)$$

where $w_j$ is the weight of the $j^{th}$ PM probe. As a metric for overall quality of, i.e., confidence in, a given chip, either the median or $75^{th}$ percentile of the relative weight factor (RWF) determined for all transcripts across the chip can be used. RWF is the weight factor for a given fragment relative to the median weight factor for that fragment as determined by the model. RMA may also be useful for detecting thin artifacts such as scratches, which tend to be problematic for many other metrics.

In addition to (1.) Median of RWF and (2.) $75^{th}$ percentile of RWF, the following metrics can be derived using RMA analysis:

3. Horizontal (and vertical) variance of weights: The variance values are determined by $$\frac{\left(\sum_{x}(x_x - \mu)^2\right)}{(N-1)}, \quad (25)$$

where $x_x$ is the sum of the weights in column (row) x and $\mu$ is the mean of these sums. N is the number of columns (rows). This metric is useful for flagging local defects.

$$4. \sum_j \sum_k w_{jk}^{-1}, \forall j, k, \quad (26)$$

where $w_{jk}$ is the weight of the $j^{th}$ PM probe of transcript k. The sum of the inverse weights can be used as an indicator of overall chip quality. The higher this value, the lower the quality of the chip.

$$5. \sum_j \sum_k w_{jk}^{-2}, \forall j, k, \quad (27)$$

where $w_{jk}$ is the weight of the $j^{th}$ PM probe of transcript k. This value is also useful as an indicator of overall chip quality.

$$6. \sum_j \sum_k (1 - w_{jk}), \forall j, k, \quad (28)$$

where $w_{jk}$ is the weight of the $j^{th}$ PM probe of transcript k can be used as an indicator of overall chip quality.

7. Profile of Normalization Distortion Percentiles. These are the $5^{th}$ through $95^{th}$ percentiles (in increments of 5) of the discrepancies between the normalized and non-normalized PM probe values, which can be used to measure the negative effects of normalization.

8. MAS5 Log Ratios. While not strictly RMA, using MAS 5.0 measurements from the database, a matrix is constructed for each chip type. The rows are the transcripts for that chip and the columns are the SNOMED (Systematized Nomenclature of Medicine) codes for each tissue. The matrix entries are the median for all available samples (if less than 40), or randomly selected forty (40) samples, MAS 5 values for each corresponding transcript, tissue, and chip type. For each sample array, the MAS5 value for each transcript is compared with the matrix value for the given transcript, tissue, and chip type and the log of the ratio determined. The median and interquartile range (IQR) is determined, for these log-ratios, across the transcript on the microarray. The sum of the median and IQR is the MAS5 Total Error, which is recorded, along with the median and IQR, for each chip. This value can be used to flag problems with the MM probes.

9. Gravity model metrics for clusters: These metrics can be used to detect clusters of bad probes (due to local defects) and have the following forms.

$$\Sigma((w_p w_q)^{-1}/(\text{Euclid}(p,q))^2), \forall p \neq q, \text{ or} \quad (29)$$

$$\Sigma((1-w_p)(1-w_q)/(\text{Euclid}(p,q))^2), \forall p \neq q, \quad (30)$$

where p and q are 2D vectors, each giving the Cartesian coordinates of the PM probes over all the transcripts. Euclid( ) signifies the Euclidean distance between the arguments.

The calculated metrics for each chip are recorded in a database and are available to the QC operator to assist in evaluating the quality of the chips. A bit flag field, IP_Fail-Flags records whether or not each metric falls within the acceptable range for each chip. The image processing program which computes the metrics, autoqc.exe, runs preferably as a batch overnight job on all images ready to be QCed. Later, the IPLimits program computes IP_FailFlags 28 and records the results in the database. Chips that pass all the metrics have an IP_FailFlags of 0. Other chips have one or more of the bits set and also have a description of the possible defects based on the failed metrics (IP_FailDescription).

The Probe Pair Difference (PPD) algorithm (see metric 8 in Table A) fits the intensity (perfect-match minus mismatch, PM-MM) of all probe pairs for each gene set to a characteristic shape and flags probes which do not conform to the characteristic shape as P (Probe) outliers. In addition, probe pairs that vary from chip to chip to such a large extent that they cannot be included in the model at all are flagged as M (Model) outliers for that chip type. A training set of experiments containing each gene at varying intensities is used to determine the initial characteristic shape and M outliers on a chip. The different outlier types are summarized in Table B below.

TABLE B

| Outlier Type | Description |
| --- | --- |
| M | Model outliers are considered outliers for every chip of this type |
| P | Probe outliers are identified in a given chip (experiment) according to PPD and GeneChip ® algorithms or manual QC |
| Y | Probe pairs with MM > PP |
| T | outliers are identified in a given chip (experiment) according to PPD and GeneChip ® algorithms or manual QC |
| N | outliers are identified in a given chip (experiment) according to GeneChip ® algorithms or manual QC but not PPD |

The total number of P and T type outliers can provide a useful measurement of overall chip quality. In addition horizontal and vertical interval data (i.e., number of outliers in each vertical or horizontal strip) can be used to identify defect regions and grid misalignment. Average intensity measurements of the entire chip, the spike-ins and one of the controls (OligoB2) provide a first-pass evaluation of the overall quality of the chip.

Figure 3:
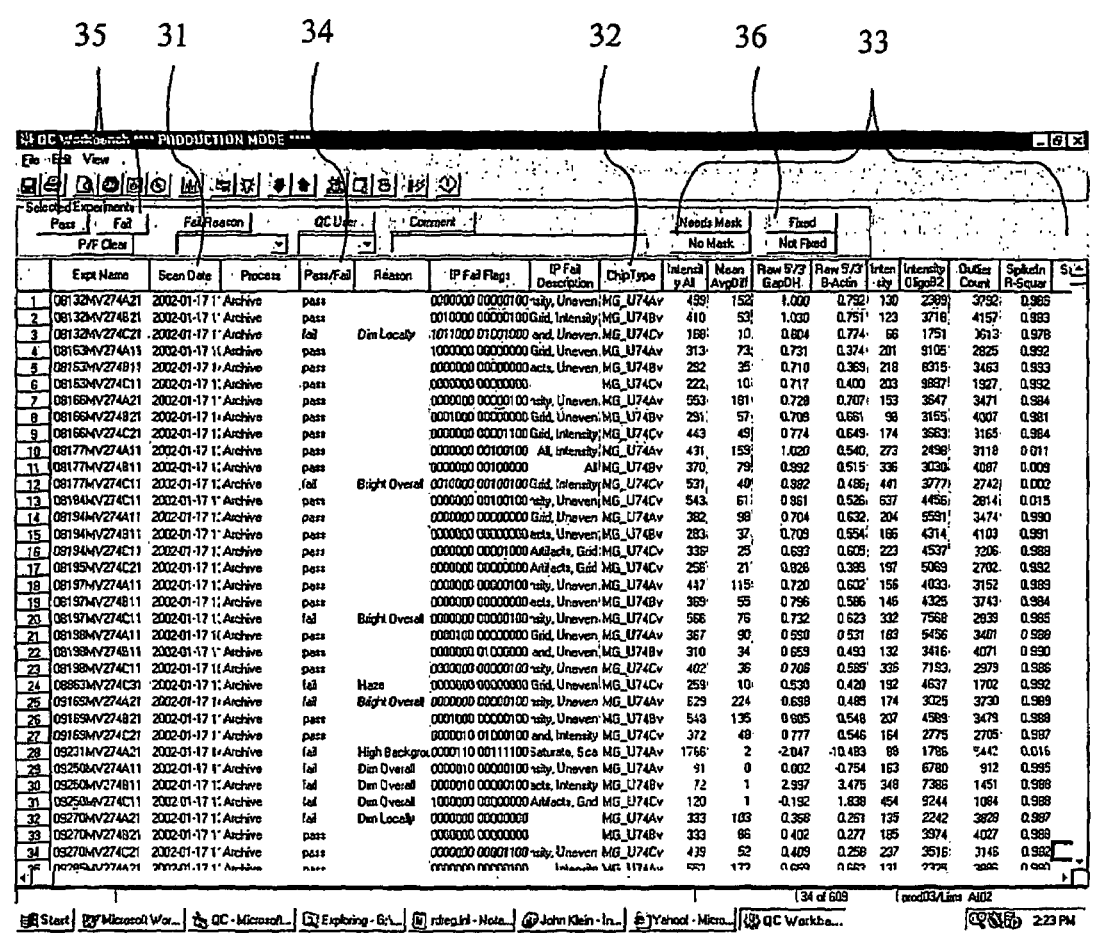

Referring to FIG. 3, an embodiment of the present invention includes a centralized application for managing the QC process. The embodiment enables a user to query based on chip parameters such as scan date 31, chip type 32, lot number, IP metrics 33, pass/fail status 34 or a combination of these parameters. A list of chips meeting the query criteria is then displayed in a flexible grid along with the image parameters (for example, 60 columns). Users can manipulate the display by hiding, rearranging and/or sorting columns. Pass/Fail status, defects (if any) and QC image processing data include some of the displayed columns. The image viewing application and the masking applications can be invoked from the centralized application. The grid can be copied to the clipboard or printed. Functions include: 1) View Images (invoking Affymetrix® Microarray Suite (MAS))—multiple images can be opened simultaneously by multi-selecting them in the grid and clicking the MAS toolbar button; 2) Also through MAS, grids can be realigned and new CEL files can be generated from DAT files; 3) Mask (invoking Affymetrix-.exe)—An image can be opened by selecting it and then clicking the Masking toolbar button; 4) Set Pass Fail status—Can be set a row at a time by the dropdown or for multiple rows by multi-selecting and clicking the Pass or Fail button 35. In one embodiment of the present invention, the pass/fail status of a chip can be revised even after it has been set, as long as the chip has not yet been analyzed (or published or archived); 5) View image processing information including metrics and limits; 6) View chips' history. This can be done by selecting the "History" checkbox 41 on the Filter screen (FIG. 4); 7) View problems; 8) Mark problems as corrected; 9) Set "Needs Mask" flag; 10) View which chips' CEL files have masks; and 11) Generate IP metrics and limits—in the case where new CEL files need to be generated.

The grid can be sorted by any column, and columns can be rearranged. Examples of grid columns include: 1) Pass/Fail—current status of pass fail in the database. This parameter can be set individually by chip or for multiple chips by highlighting and clicking on the Pass or Fail button 35; 2) Status—Modifiable pass/fail status—will update the database upon Save. Status defaults to "Not VQCed" before pass/fail status is assigned; 3) Problem—description of current problem if any; 4) Fixed—Fixed button 36 or status ('Fixed') for records with current problems. Upon Save, the problem will be marked as fixed by writing a new record to the ChipProcess table; 5) Needs mask—flag set by QC user indicating the image needs to be masked. Upon Save, the NeedsMask field in the Chip table will be updated and a new record will be written to the ChipProcess table with a "Needs mask" problem Id; 6) Masked—display only. Field in Chip table set by the mask application when the mask information is exported. Further embodiments include ways to handle CEL files that are masked then later deleted and a new non-masked CEL file is generated; 7) Scanner setting (High/Low)—can be used when opening Masking application; and 8) Scanner name—original scanner name.

Filters are provided to select data of a pre-determined quality based on almost all chip parameters, alone or in combination. As shown in the Filter screen shot of FIG. 4 under the category "Image Processing Parameters", a user can select one or more quality metrics to be applied by checking the desired box.

In an embodiment of the present invention, Affymetrix® MicroArray Suite (MAS) 5.0, MAS 5.0 can be invoked from the centralized application to view images. One or more chips are highlighted in the workbench, and MAS is invoked to display these images. For example, 20 images at a time can be displayed.

MAS can also be used to generate new CEL files if the old files have problems (e.g., grid misalignment) or were not generated during scan. Once new CEL files are generated, new IP metrics and limits can be calculated for the new CEL files through the centralized application of the present invention.

The masking program is used to mask small defective regions in an otherwise good chip. In one embodiment, a chip is highlighted and masking is invoked to display the image. One or more rectangular or elliptical, or other shaped masks can be added along with the defect type for each mask. Once completed, a new CEL file is generated containing the masked cells. The defect information is also stored in the Defect and Defect_ROI tables. Since only passed chips need to be masked, the pass/fail status is set to pass.

The ChipDefects database is used for QC information. The Chip table contains one record for each chip. The ChipProcess table tracks each process a chip goes through during the QC process. The Defect and Defect_ROI table contain information each masked region.

FIGS. 4A-F combine to provide a spreadsheet illustrative of an embodiment of the present invention. Referring to FIG. 4A, the listed chips come from two sites (A and B) 401 and there are 15 chips per site. By reviewing the metrics, there are two chips 402, 403 that stand out. The first chip 402 is out of range on 5 metrics ("IP Fail Count") 404 while other chips from the same site failed 3 or less. Because only 5 metrics failed, the kinds of metrics that failed are analyzed. A review of FIGS. 4A-F reveal that many of the out of range metrics have "top" or "left" in their names. This information suggests that 1) this chip 402 is most likely to be an outlier among site A's dataset, and 2) the problem with the chip 402 is most likely in the top left region of the image.

The second chip 403 identified is out of range on 11 metrics while others from the same site only failed 2 or less. Without proceeding further, there is high confidence that this chip has problems. Apparent in a review of the metrics is that the overall brightness of the chip, "Intensity All" 405, and the background "Image 5%" 406 are higher than any of the other chips at either site.

Overall, both sites appear to perform similarly. Most of the chips are out of range on only 0-2 metrics. The data analysis for this project confirms that chips 402 and 403 are outliers and that the rest of the data is overall very comparable.

As chips move from scanning through the QC Process they go through most of the steps listed in the embodiment shown in FIG. 1: Validate, ImageProcess, Visual QC, (Mask), Analysis, (Import), ValidateChp, Publish, Archive. Each step that a chip experiences is recorded in the Chip Process table, FIG. 5, along with any problems and fixes. Each record contains the experiment name, the process, a problem Id (or 0(zero) if no problem), the user, the date/time and a Current/History flag. Filename is also a field that records the filename in the Analysis or Import step. Rather than updating the existing records, new records are inserted with the Current/History flag set to CURRENT. Any existing records with the same experiment name have their Current/History flag set to HISTORY.

Each QC process inserts a record as a chip is processed. Records contain experiment name, processed, operator, date/time, problemid and a current/history flag. This creates an audit trail of each chip's history. Import and Analysis processes also contain the filename in the Filename column.

Two controlled vocabulary tables are CV_PROCESS, FIG. 6, and CV_PROBLEM, FIG. 7. In one embodiment, CV_PROCESS contains an ID and description of all processes in QC. Other embodiments have other fields to control the workflow. CV_Problem contains Id and description of all problems. Other embodiments have additional fields containing severity information (e.g., warning, error, fatal error).

As shown in FIG. 8, the Chip table (VQC Pass/Fail) contains fields relating to a chip as it goes through the QC process. These include the experiment name, pass/fail status, fail reason, pass/fail date, and all the image processing metrics and limits data. The NeedsMask field can be set to indicate that a chip should be masked, and the Masked field indicates that an image has been masked.

In one embodiment, records are inserted into the Chip table during the Image Processing step when the IP metrics are computed. The Visual QC process then updates the record with pass/fail status and other information. However, there may be times when processes are done out of order or repeated, so it is important for processes to check the experiment name to determine if a chip is already in the Chip table before inserting a record. The ExperimentName column has a Unique constraint.

The Defect and Defect ROI tables may be considered one table and are divided only for historical reasons. The primary key, Defect Id, links the two tables. The DEFECT table, FIG. 9, contains one record for each masked region and is linked to the Chip table by the foreign key field, ChipId. This table contains the defect description. The DEFECT_ROI (defect region of interest) table, FIG. 10, also contains one record for each defect and is also linked to the Chip table through a ChipId foreign key. This table contains the masked shape (rectangle or ellipse) and the left, right, top, and bottom of the defect in both image (DAT file) and grid (CEL file) coordinates.

FIG. 11 provides an example of a table containing a list reasons for failing a chip or for masking a region.

With the addition of the ChipProcess table, several triggers have been added to the database. CHIP_PROCESS_INS_TR executes before insert into the ChipProcess table. This function checks to see if there is an existing record in ChipProcess with the same ExperimentName as the new record. If so, it uses the ChipId field from the existing record in the new record. If not, it uses ChipId_Seq.Next. CHIP_PROCESS_INS_TR also changes the History field of all existing records with the same ExperimentName to 'HISTORY' and sets the field to 'CURRENT' in the new record.

CHIP_PROCESS_DEL_TR executes before delete on the ChipProcess table. If the deleted record has a 'CURRENT' History field, this function updates the most recent previous record (using the Date/Time field) having the same ExperimentName, if any, to 'CURRENT'.

Several ChipDefects tables contain information on the image processing metrics and limits:

IP_METRICS—the metric name and bit position (if any) in IP_FailFlags

IP_TESTLIMITS—upper and lower limits of metrics, by chip type and scanner setting IP_DEFECT—List of possible defects detected by the metrics IP_METRIC_DEFECTS—Associates metrics with defects IP_KNOWN—chip types that have metric limits. It takes a while for limits to be developed for new chip types.

IP_LIMITSVERSION—Version of the limits used to calculate the fail bits. Versions may be updated as limits change as more data is generated and evaluated.

Information from several tables in the Affymetrix® ProcessDB database are also used by an embodiment of the present invention. These tables are accessed via a database link to ProcessDB. In addition the CHIP_HYB_SCAN_INFO table in the CC_CHECK schema is updated on a regular basis during batch processing, which typically will be performed overnight when user demand is low, and contains scanner and fluidics information. All these tables are accessed through a database link to the Affymetrx® LIMS 3 Oracle for instance. The different fields used by the present invention are shown in FIG. 12.

Figure 13:
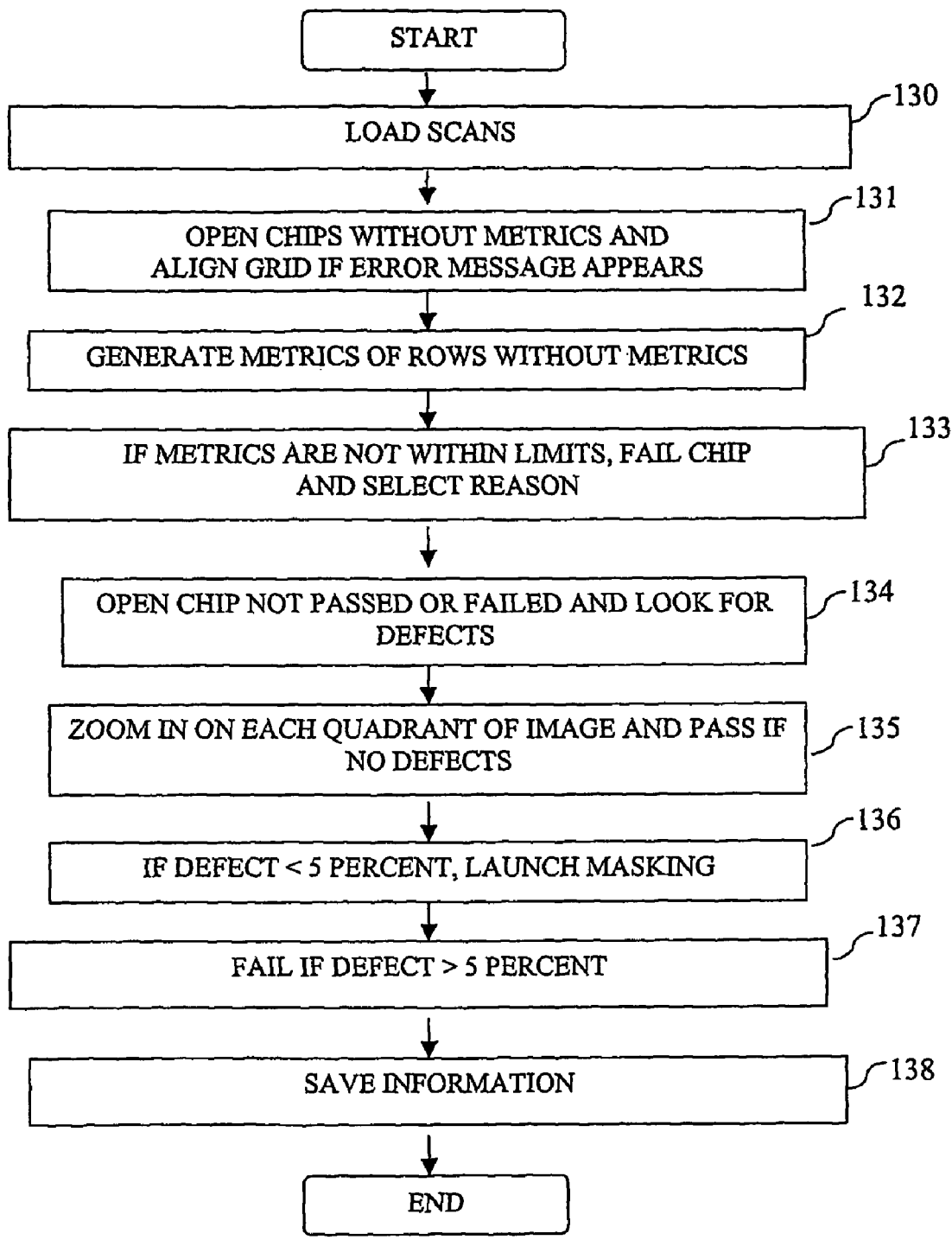
FIG. 13 is a process flow diagram for an embodiment of the present invention.

FIG. 13 illustrates the process flow of an embodiment of the present invention. The process comprises the following steps: Launch the centralized application and load with the previous day's scans 130; Open chips without metrics and align the grid if an error message appears stating the grid needs alignment 131 (see Affymetrix® MAS 5.0 User Guide, incorporated herein by reference, for grid alignment instructions); Generate metrics of the rows without metrics 132; If the metrics are not within the limits (numbers are red), then fail the chip and select the appropriate reason for failure 133; Open the chips listed on the centralized application which have not been passed or failed and visualize by looking for defects 134; Zoom in on each quadrant of the image (see Affymetrix® MAS 5.0 User Guide), pass if no defects are seen 135; If there is a defect which is less than five percent of the image, then launch masking program 136; Fail if the defect is greater than five percent 137; and Save information on the centralized application 138.

Hardware embodiments for the process of FIG. 13 include designated QC computer work stations in the analysis room. Additional software may include, for example, a masking program (such as QUALMS, Gene Logic Inc., Gaithersburg, Md. USA), Affymetrix® Microarray Analysis Suite (MAS), and automated quality control program (such as autoqc.exe Gene Logic Inc., Gaithersburg, Md. USA).

Figure 14:
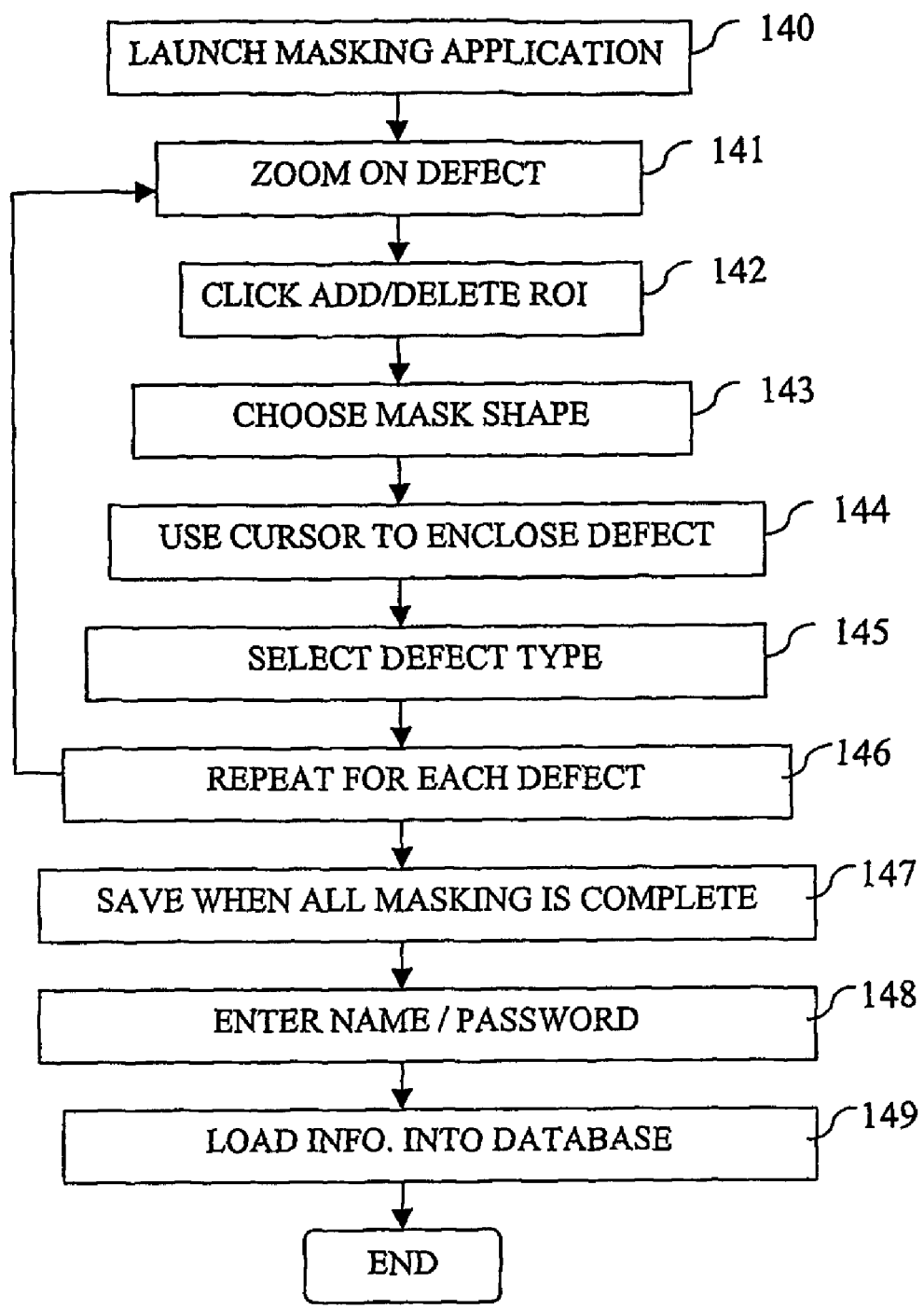
FIG. 14 is a process flow diagram for masking defective areas on a chip for an embodiment of the present invention.

FIG. 14 illustrates a process of an embodiment of the present invention to mask defective areas on a chip. The process comprises: Launch, for example, a masking application from the centralized application of the present invention 140; Zoom in on the defect 141, for example, by clicking on "zoom," then move the cursor to the defect and left click to zoom in—Right click to zoom out; Click on "Add/Delete ROI" 142; Click on "Ellipse" or "Rectangle" to choose the mask shape 143; Click to the upper left of the defect, then drag the cursor to the lower right and click again to make the ellipse or rectangle enclose the defect 144; A box will pop up which says "Defect Type"—Choose from the scroll down list, the best description of the defect 145; Repeat the process 146 beginning at 141 above for each defect on the chip; To remove an ellipse or rectangle, click on "Add/Delete ROI" and then right click on the desired area; Click on "Export" to save when all of the masking is complete for this chip 147; Enter the operator name and password as directed by the screen and click "OK" 148; Click on "Save" on the next prompt to load this information into the database 149; and Click "End" when the original screen returns.

A further embodiment of the present invention involves a software application accessing a database that stores all of the information, all of the paths found, all of the metrics, and all of the thresholds; and then initiates some user interaction, for example, allowing manual override of a pass/fail. This provides, in essence a data management application.

An aspect of the present invention involves taking each individual chip and calculating the series of metrics for that chip. For example, with thirty separate numbers for a chip, based on those thirty numbers for each particular chip type, there is a set of thresholds. For each metric, there may be an upper acceptable limit and a lower acceptable limit (see, e.g., "Image Processing Parameters" in FIG. 4). There may also be a type of a hierarchy of metrics such that for certain metrics, an out of range chip will be automatically failed while for others, it may act only as a warning, triggering manual inspection of those chip. Accordingly, in an embodiment of the present invention, a manual component remains.

In a further embodiment, the inventive methodology may be written in a Visual Basic program accessing an Oracles database where all the metrics are stored. When a new chip is released, for example, from Affymetrix®, an embodiment of the invention runs through the process of defining with new metrics, or reusing the old metrics but defining new thresholds.

In an additional embodiment, if a metric is determined to be relatively unreliable a predictor of quality of the chip, it is usually assigned a lower weight, however is not dropped entirely. Further, if a metric has a tendency to flag chips that are actually passing, one option is to expand the threshold for passing and failing, then periodically assess whether the threshold requires further adjustment because too many are failing or too many are passing.

In some instances, the scanner may be the source of variability. The same metrics may be used to validate the scanner. The metrics as a whole are useful for identifying variability of the scanners and separate metrics may also be developed for the scanner. Occasionally, for example, when a scanner validation process is performed and one metric appears to be very good at highlighting differences between scanners, this may lead to the metric being assigned increased weight in the quality control process. Without the present invention, the QC process slows down significantly and accuracy suffers in terms of judgment made on chip quality.

Once all the metrics have been run on the chips, the output is visually presented on a suitable display. Each row in the listing represents one chip that has been scanned. Moving across the row is either various information about that chip, or further to the right, some of the actual metrics.

In another embodiment, metrics that are flagged can be displayed using some form of highlighting, such as causing the flagged metrics to appear red in color on the graphical user interface (GUI) display screen. This allows the user to readily identify the metrics that stand out. Further embodiments may provide a summary of how many metrics for a given chip have failing values. For example, the probes that fall outside of a certain brightness range may fail, while others that are more marginal may require researchers to visually observe the result.

In an embodiment of the present invention, the data may be saved permanently in a large database. One storage scheme is cumulative: as more data is saved to the database, the database dynamically builds on the new data. An alternate embodiment does not utilize a dynamic process, however, the database allows researchers to access stored information such as historical numbers and process control variations, allowing the values for the various metrics to be viewed for changes with time.

An embodiment of the present invention collects, for example, Affymetrix® information and enters it into the database. Each individual spike and its intensity are required to be provided in reports that are generated by Affymetrix® MAS. (Affyimetrix provides the software for generating reports which are then returned to Affymetrix)

The Affymetrix® Laboratory Information Management System (LIMS) is a database that captures information about the scanned chips and related processes in the lab. LIMS captures data on how the chips are run, how they were scanned on the scanner, which scanner, etc. The MAS software provides instrument control for the scanner, array image acquisition and analysis, and communicates with the LIMS software. After the chip is scanned, the MAS updates LIMS by publishing gene expression data and sample history, and monitoring and providing experiment protocols and conditions.

Another embodiment of the present invention functions independently of MAS. In this embodiment, the tissue is managed by LIMS from the time it goes on the chip up until the QC step. The present invention performs the QC procedure then, downstream, the QC LIMS resumes control to perform the analysis and publishing.

A further embodiment of the present invention allows a specific chip to be selected for display, for example, on a computer monitor. Through the use of a pointing device (mouse, track ball, touch screen, etc.) controlling a cursor on the display screen, for example, a button (link) is selected to open up the record for the chip in MAS so that the operator can view the actual scanned image. Accordingly, an embodiment of the present invention interacts with MAS Therefore, instead of physically handling the chip or physically analyzing the chip, visual inspections may be made through the present invention.

Figure 4:
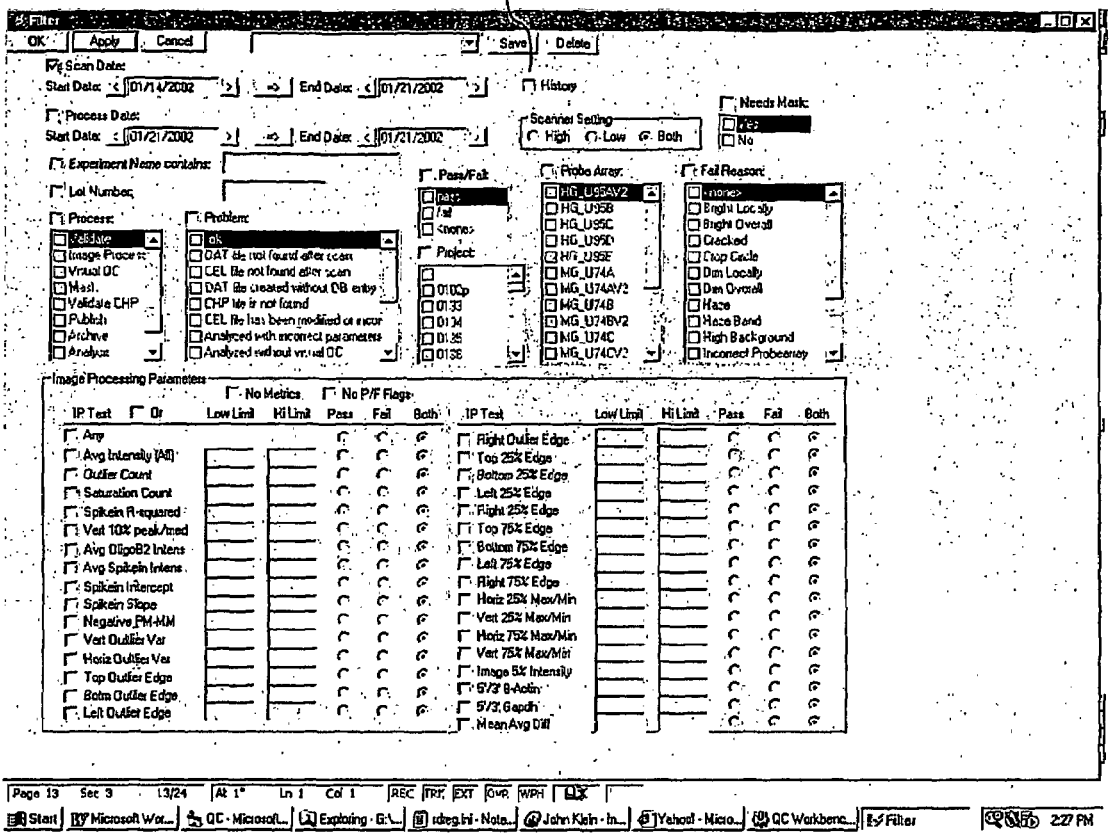
FIG. 4 is an exemplary screen shot of a filter screen of an embodiment of the present invention.

The operator can view all the chip data and select which data records to open. Multiple chip data records may be opened at a time. The selection of particular data, in a further embodiment, is handled through a filter window, such as shown in FIG. 4. The filter window allows the operator to select the desired data from the database. For example, the desired data may be for chips scanned during a certain date range, or the user may wish to view only passing chips, or only failing chips. For each of the metrics, specific ranges may be selected, and, if desired, the user can select one or specific metrics. As a result, the operator can selectively view the chips that fall within the desired range on a given metric.

The preceding embodiment is particularly useful for researchers wishing to redefine the threshold limits. A researcher can review the threshold limits at a certain point, then determine how many pass and how many fail, as opposed to, setting it at another level. The threshold limits may change from chip to chip, however all of the metrics are designed to be calculated on every type of chip set. The present invention is not chip set specific and, therefore can be universally applied.

Even if chips are processed differently, the metrics themselves may still be useful. For example, the thresholds for brightness may be tied to the manner in which the chips are processed even when there should be little deviation in chip processing. Therefore, this embodiment would be useful in assessing changes in chip characteristics related to changes in processing. The metrics can help identify what changes are occurring and whether they might affect the resulting expression data Such metrics will be an important factor in the identification of specific ranges.

In addition, different limits can be assigned for each array type. Such metrics will be taken in combination with other factors, for example, whether a group of samples was processed on a given day, or whether they were scanned using a different scanner. The Affymetrix® database will include data identifying the scanner that was used to scan a given chip, the dates and times when the chip was scanned, etc., however, the Affymetrix® data will not include information about the sample or any processing that may have occurred prior to placing the sample onto the chip.

In accordance with an embodiment of the present invention, visual inspection can occur using a computer generated image, rather than directly inspecting the chip set itself. Often, physical defects such as scratches are impossible to see physically. Many of the problems that occur relate to how well the chip is stained. To evaluate this parameter, the fluorescence on the chip must be observed. Accordingly, in an embodiment of the present invention, fluorescence can be viewed as a variety of colors displayed on the computer display screen.

The system and method of the present invention provide a means by which gene expression data obtained from microarrays can be automatically screened for quality using a number of different metrics selected to identify commonly occurring defects. This screening process maximizes integrity of the data and provides means by which a system user can select data according to his or her specific quality standards.

The foregoing examples are provided by way of explanation of the invention, not as a limitation of the invention. It will be apparent to those skilled in the art that various modifications and variations can be made in the present invention without departing from the scope or spirit of the invention. For instance, features illustrated or described as part of one embodiment can be used on another embodiment to yield a still further embodiment. Thus, it is intended that the present invention cover such modifications and variations that come within the scope of the appended claims and their equivalents.

What is claimed is:

1. A method for analyzing gene expression data obtained from a plurality of microarrays having a plurality of probes, wherein the plurality of probes includes mismatch (MM) probe pairs having a mismatch value and perfect match (PM) probe pairs having a perfect match value, the method comprising the steps of:

obtaining image data corresponding to scanned microarrays, the image data for each scanned microarray comprising an image corresponding to the scanned probe intensities, scan date, and at least one chip identifier;

storing the image data for each scanned microarray in at least one database;

applying an automated quality control process, comprising the steps of in a processor, processing the image data by applying at least a portion of a plurality of image processing metrics comprising algorithms adapted to identify one or more defects selected from the group consisting of haze, bright artifacts, dim artifacts, crop circles, snow, misalignment, grid misalignment, high background intensity, saturation, scratches, cracks;

flagging any identified defects;

assigning a pass/fail status to each microarray based upon identified defects, if any;

storing the processed image data in the at least one database, the processed image data comprising the scanned probe intensities, the scan date, the at least one chip identifier, the pass/fail status, the applied image processing metrics, and the identified defects, if any;

providing a user interface for searching the at least one database by selecting at least one chip parameter from the group consisting of scan date, the at least one chip identifier, the pass/fail status and the plurality of image processing metrics; and displaying the results of the search.

2. The method of claim 1, wherein the step of processing the image data further comprises applying a mask to exclude data corresponding to defects.

3. The method of claim 1, wherein an image processing metric of the plurality comprises counting the MM probe pairs and PM probe pairs and flagging a microarray as dim if the number of MM probe pairs is greater than the number of PM probe pairs.

4. The method of claim 1, wherein an image processing metric of the plurality comprises determining a normalized background variance by estimating a local background intensity and its spatial variation at a plurality of locations on the microarray corresponding to PM probes.

5. The method of claim 1, wherein an image processing metric of the plurality comprises:

estimating a local background intensity at a plurality of locations on the microarray corresponding to perfect match (PM) probe pairs;

dividing the microarray into inner and outer portions;

determining a mean background intensity for each of the inner and outer portions; and using a ratio of mean background intensities of the outer and inner portions to flag crop circles.

6. The method of claim 1, wherein an image processing metric of the plurality comprises:

generating a model using the PM probe pairs from a set of microarrays; applying the model to each microarray to be analyzed to determine a weights factor for each probe on the microarray.

7. The method of claim 1, wherein the defect is haze and the image processing metric is selected from the group consisting of vertical $10^{th}$ percentile peak to median ratio, maximum/minimum ratio for horizontal $25^{th}$ percentile profile, two edge ratios for horizontal $25^{th}$ percentile profile, two edge ratios for vertical $25^{th}$ percentile profile, maximum/minimum ratio for horizontal $75^{th}$ percentile profile, and two edge ratios for horizontal $75^{th}$ percentile profile.

8. The method of claim 1, wherein the defect is bright artifacts and the image processing metric is selected from the group consisting of oligo B2 mean intensity, spike-in offset, spike-in coefficient of determination, two edge ratios for horizontal $25^{th}$ percentile profile, two edge ratios for vertical $25^{th}$ percentile profile, two edge ratios for horizontal $75^{th}$ percentile profile, probe pair difference outlier horizontal variance, vertical probe pair difference outlier, negative probe pair horizontal and vertical variance, negative probe pair horizontal and vertical maximum/minimum ratio, local background normalized variance.

9. The method of claim 1, wherein an image processing metric of the plurality comprises a ratio of the natural log of a mean intensity of non-control oligonucleotides to the natural log of an image fifth percentile.

10. An automated system for analyzing gene expression data obtained from a plurality of chips having a plurality of probes, wherein the plurality of probes includes mismatch (MM) probe pairs having a mismatch value and perfect match (PM) probe pairs having a perfect match value, the system comprising:
- a database for storing image data for a plurality of scanned chips comprising an image corresponding to scanned probe intensities and a plurality of chip parameters corresponding to the scanned chip, wherein the chip parameters are selected from a group consisting of scan date, chip type, lot number, image processing metrics, and pass/fail status;
- a user interface for receiving a user query comprising at least one chip parameter and for displaying information responsive to the query;
- a processor for processing the image data for quality control by applying at least one of a plurality of image processing metrics adapted to identify defects selected from the group consisting of haze, bright artifacts, dim artifacts, crop circles, snow, misalignment, grid misalignment, high background intensity, saturation, scratches, cracks, and for searching the database for records corresponding to the selected at least one chip parameter.

11. The system of claim 10, wherein the processor is further operable to apply a mask to exclude data corresponding to defects.

12. The system of claim 10, wherein an image processing metric of the plurality comprises counting the MM probe pairs and PM probe pairs and flagging a microarray as dim if the number of MM probe pairs is greater than the number of PM probe pairs.

13. The system of claim 10, wherein an image processing metric of the plurality comprises determining a normalized background variance by estimating a local background intensity and its spatial variation at a plurality of locations on the microarray corresponding to PM probes.

14. The system of claim 10, wherein an image processing metric of the plurality comprises:
- estimating a local background intensity at a plurality of locations on the microarray corresponding to perfect match (PM) probe pairs;
- dividing the microarray into inner and outer portions;
- determining a mean background intensity for each of the inner and outer portions; and
- using a ratio of mean background intensities of the outer and inner portions to flag crop circles.

15. The system of claim 10, wherein an image processing metric of the plurality comprises:
- generating a model using the PM probe pairs from a set of microarrays; applying the model to each microarray to be analyzed to determine a weights factor for each probe on the microarray.

16. The system of claim 10, wherein the defect is haze and the image processing metric is selected from the group consisting of vertical $10^{th}$ percentile peak to median ratio, maximum/minimum ratio for horizontal $25^{th}$ percentile profile, two edge ratios for horizontal $25^{th}$ percentile profile, two edge ratios for vertical $25^{th}$ percentile profile, maximum/minimum ratio for horizontal $75^{th}$ percentile profile, and two edge ratios for horizontal $75^{th}$ percentile profile.

17. The system of claim 10, wherein the defect is bright artifacts and the image processing metric is selected from the group consisting of oligo B2 mean intensity, spike-in offset, spike-in coefficient of determination, two edge ratios for horizontal $25^{th}$ percentile profile, two edge ratios for vertical $25^{th}$ percentile profile, two edge ratios for horizontal $75^{th}$ percentile profile, probe pair difference outlier horizontal variance, vertical probe pair difference outlier, negative probe pair horizontal and vertical variance, negative probe pair horizontal and vertical maximum/minimum ratio, local background normalized variance.

18. The system of claim 10, wherein an image processing metric of the plurality comprises a ratio of the natural log of a mean intensity of non-control oligonucleotides to the natural log of an image fifth percentile.

19. A computer readable medium having stored thereon one or more sequences of instructions for causing one or more microprocessors to perform the steps for determining quality of a microarray comprising a plurality of probes including PM probes, the steps comprising:
- in a set of microarrays comprising a plurality of transcripts, determining a probe weight for each PM probe using RMA analysis; and
- calculating a relative weight factor for each transcript by taking the inverse of the square root of the sum of the probe weights for each PM probe;
- wherein a higher relative weight factor value corresponds to a lower quality microarray.

20. The computer readable medium of claim 19, wherein RMA analysis comprises:
- background correcting a PM probe value for each PM probe;
- $\log_2$ transforming the background-corrected PM probe values;
- quantile normalizing the $\log_2$ transformed probe values for the set of microarrays; and
- applying median polish to the quantile normalized values to obtain the probe weight for each PM probe.

21. A computer readable medium having stored thereon one or more sequences of instructions for causing one or more microprocessors to perform the steps for determining quality of a microarray comprising a plurality of probes including PM probes, the steps comprising:
- in a set of microarrays comprising a plurality of transcripts, determining a probe weight for each PM probe using RMA analysis; and
- calculating a quality metric according to the relationship:

$$\bar{w} = \frac{1}{\sqrt{\sum_{j=1}^{J} w_j}},$$

where $w_j$ is the weight of the $j^{th}$ PM probe.

22. The computer readable medium of claim 21, wherein RMA analysis comprises:
- background correcting a PM probe value for each PM probe;
- $\log_2$ transforming the background-corrected PM probe values;
- quantile normalizing the $\log_2$ transformed probe values for the set of microarrays; and
- applying median polish to the quantile normalized values to obtain the probe weight for each PM probe.

23. A computer readable medium having stored thereon one or more sequences of instructions for causing one or more microprocessors to perform the steps for determining quality of a microarray comprising a plurality of probes including PM probes, the steps comprising:

in a set of microarrays comprising a plurality of transcripts, determining a probe weight for each PM probe using RMA analysis; and calculating a quality metric according to the relationship:

$$\sum_j \sum_k w_{jk}^{-x}, \forall\, j, k,$$

where $w_{jk}$ is the weight of the $j^{th}$ PM probe of transcript k, and x=1 or 2.

24. The computer readable medium of claim 23, wherein RMA analysis comprises:
  background correcting a PM probe value for each PM probe;
  $\log_2$ transforming the background-corrected PM probe values;
  quantile normalizing the $\log_2$ transformed probe values for the set of microarrays; and
  applying median polish to the quantile normalized values to obtain the probe weight for each PM probe.

25. A computer readable medium having stored thereon one or more sequences of instructions for causing one or more microprocessors to perform the steps for determining quality of a microarray comprising a plurality of probes including PM probes, the steps comprising:

in a set of microarrays comprising a plurality of transcripts, determining a probe weight for each PM probe using RMA analysis; and calculating a quality metric according to the relationship:

$$\sum_j \sum_k (1 - w_{jk}), \forall\, j, k,$$

where $w_{jk}$ is the weight of the $j_{th}$ PM probe of transcript k.

26. The computer readable medium of claim 25, wherein RMA analysis comprises:
  background correcting a PM probe value for each PM probe;
  $\log_2$ transforming the background-corrected PM probe values;
  quantile normalizing the $\log_2$ transformed probe values for the set of microarrays; and
  applying median polish to the quantile normalized values to obtain the probe weight for each PM probe.

* * * * *